US009556432B2

United States Patent
Hussain et al.

(10) Patent No.: US 9,556,432 B2
(45) Date of Patent: Jan. 31, 2017

(54) METHOD OF TREATING HYPERLIPIDEMIA AND ATHEROSCLEROSIS WITH MIR-30C

(71) Applicant: THE RESEARCH FOUNDATION FOR THE STATE UNIVERSITY OF NEW YORK, Albany, NY (US)

(72) Inventors: Mahmood Hussain, Woodbury, NY (US); James Soh, Brooklyn, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/370,846

(22) PCT Filed: Jan. 9, 2013

(86) PCT No.: PCT/US2013/020718
§ 371 (c)(1),
(2) Date: Jul. 7, 2014

(87) PCT Pub. No.: WO2013/106358
PCT Pub. Date: Jul. 18, 2013

(65) Prior Publication Data
US 2014/0336240 A1 Nov. 13, 2014

Related U.S. Application Data

(60) Provisional application No. 61/584,958, filed on Jan. 10, 2012.

(51) Int. Cl.
A61K 48/00 (2006.01)
C07H 21/02 (2006.01)
(Continued)

(52) U.S. Cl.
CPC .......... C12N 15/113 (2013.01); A61K 31/713 (2013.01); A61K 45/06 (2013.01); G01N 33/5023 (2013.01);
(Continued)

(58) Field of Classification Search
USPC .......................................... 514/44; 536/24.5
See application file for complete search history.

(56) References Cited

U.S. PATENT DOCUMENTS 5,223,409 A 6/1993 Ladner et al.
5,399,346 A 3/1995 Anderson et al.
(Continued)

FOREIGN PATENT DOCUMENTS

WO WO 2009/085234 A2 7/2009
WO WO 2011/103135 A1 8/2011

OTHER PUBLICATIONS

*Homo sapiens* microRNA 30e (MIR30E), microRNA (MI0000749) NCBI Reference Sequence: NR_029846.1, downloaded from http://www.ncbi.nlm.nih.gov/nuccore/NR_029846.1 on Jan. 15, 2016.*

(Continued)

*Primary Examiner* — Terra C Gibbs
(74) *Attorney, Agent, or Firm* — Scully, Scott, Murphy & Presser, P.C.

(57) ABSTRACT

This disclosure provides a novel role for microRNA (miR) regulation of lipid metabolism via the MTP pathway, leading to reductions in apoB secretion and blood lipid levels. MiR regulation of the MTP pathway is shown herein to reduce hyperlipidemia and atherosclerosis in vivo. Therefore, inhibition of MTP expression and activity by miR regulation is identified as a new therapeutic target for treatment of cardiovascular disease and conditions or diseases associated with cardiovascular disease such as hyperlipidemia, athero- (Continued)

sclerosis, and metabolic syndrome. Treatment of cardiovascular disease and associated conditions or diseases with the novel MTP inhibitors of the invention, such as miR-30c homologs or miR-30c agonists, reduces MTP-associated lipid production without side effects that occur with other methods of MTP inhibition.

18 Claims, 10 Drawing Sheets

(51) Int. Cl.

| | | |
|---|---|---|
| C07H 21/04 | (2006.01) | |
| C12N 15/11 | (2006.01) | |
| C12N 15/113 | (2010.01) | |
| A61K 45/06 | (2006.01) | |
| A61K 31/713 | (2006.01) | |
| G01N 33/50 | (2006.01) | |

(52) U.S. Cl.
CPC ..... C12N 2310/141 (2013.01); C12N 2320/31 (2013.01); G01N 2500/10 (2013.01)

(56) References Cited

U.S. PATENT DOCUMENTS

| | | |
|---|---|---|
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,489,677 A | 2/1996 | Sanghvi et al. |
| 5,519,126 A | 5/1996 | Hecht |
| 5,519,134 A | 5/1996 | Acevedo et al. |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,591,722 A | 1/1997 | Montgomery et al. |
| 5,596,086 A | 1/1997 | Matteucci et al. |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,646,265 A | 7/1997 | McGee |
| 5,656,611 A | 8/1997 | Kabanov et al. |
| 5,658,873 A | 8/1997 | Bertsch-Frank et al. |
| 5,670,633 A | 9/1997 | Cook et al. |
| 5,677,439 A | 10/1997 | Weis et al. |
| 5,700,920 A | 12/1997 | Altmann et al. |
| 5,753,613 A | 5/1998 | Ansell et al. |
| 5,785,992 A | 7/1998 | Ansell et al. |
| 5,883,109 A | 3/1999 | Gregg et al. |
| 6,066,653 A | 5/2000 | Gregg et al. |
| 6,120,798 A | 9/2000 | Allen et al. |
| 6,221,959 B1 | 4/2001 | Kabanov et al. |
| 6,346,613 B1 | 2/2002 | O'Mahony et al. |
| 6,353,055 B1 | 3/2002 | Kabanov et al. |
| 2005/0288244 A1 | 12/2005 | Manoharan et al. |
| 2006/0008822 A1 | 1/2006 | Manoharan et al. |
| 2006/0035254 A1 | 2/2006 | Manoharan et al. |
| 2006/0287260 A1 | 12/2006 | Manoharan et al. |
| 2007/0213292 A1 | 9/2007 | Stoffel et al. |
| 2009/0306181 A1 | 12/2009 | Ikeda et al. |

OTHER PUBLICATIONS

*Homo sapiens* microRNA 30c-1 (MIR30C1), microRNA (MI0000736) NCBI Reference Sequence: NR_029833.1, downloaded from http://www.ncbi.nlm.nih.gov/nuccore/NR_029833.1 on Jan. 15, 2016.*
Samaha et al. (Nature Clinical Practice, 2008 vol. 5, No. 8, pp. 497-505).*
International Search Report dated Apr. 18, 2013 issued in PCT/US2013/020718.
Liu, Yanwen et al., "Apolipoprotein B-containing lipoprotein assembly in microsomal triglyceride transfer protein-deficient McA-RH7777 cells", Journal of Lipid Research (2010), vol. 51, pp. 2253-2264.
Abell L.L. et al., "A Simplified Method for the Estimation of Total Cholesterol in Serum and Demonstration of its Specificity", J. Biol. Chem. 195:357-366 (1952).
Allain C.C. et al., "Enzymatic Determination of Total Serum Cholesterol", Clinical Chemistry 20(4):470-475 (1974).
Anderson W.F., "Prospects for Human Gene Therapy", Science 226:401-409 (Oct. 26, 1984).
Athar H. et al., "A Simple, Rapid, and Sensitive Fluorescence Assay for Microsomal Triglyceride Transfer Protein", Journal of Lipid Research 45:764-772 (2004).
Bakillah A. et al., "Measurement of Apolipoprotein B in Various Cell Lines: Correlation Between Intracellular Levels and Rates of Secretion", Lipids 32(10):1113-1118 (1997).
Bartel D.P., "MicroRNAs: Genomics, Biogenesis, Mechanism, and Function", Cell 116:281-297 (Jan. 23, 2004).
Berriot-Varoqueaux N. et al., "The Role of the Microsomal Triglyceride Transfer Protein in Abetalipoproteinemia", Annu. Rev. Nutr. 20:663-697 (2000).
Blomer U. et al., "Highly Efficient and Sustained Gene Transfer in Adult Neurons With a Lentivirus Vector", Journal of Virology 71(9):6641-6649 (Sep. 1997).
Brigham K.L. et al., "Rapid Communication: In Vivo Transfection of Murine Lungs With a Functioning Prokaryotic Gene Using a Liposome Vehicle", 298(4):278-281 (Oct. 1989).
Carell T. et al., "A Novel Procedure for the Synthesis of Libraries Containing Small Organic Molecules", Angew. Chem. Int. Ed. Engl. 33(20):2059-2061 (1994).
Carell T. et al., "A Solution-Phase Screening Procedure for the Isolation of Active Compounds from a Library of Molecules", Angew. Chem. Int. Ed. Engl. 33(20):2061-2065 (1994).
Cayouette M. et al., "Adenovirus-Mediated Gene Transfer of Ciliary Neurotrophic Factor Can Prevent Photoreceptor Degeneration in the Retinal Degeneration (rd) Mouse", Human Gene Therapy 8:423-430 (Mar. 1, 1997).
Chang B.H-J et al., "Liver-Specific Inactivation of the Abetalipoproteinemia Gene Completely Abrogates Very Low Density Lipoprotein/Low Density Lipoprotein Production in a Viable Conditional Knockout Mouse", The Journal of Biological Chemistry 274(10):6051-6055 (Mar. 5, 1999).
Chang G. et al., "Microsomal Triglyceride Transfer Protein (MTP) Inhibitors: Discovery of Clinically Active Inhibitors Using High-Throughput Screening and Parallel Synthesis Paradigms", Current Opinion in Drug Discovery & Development 5(4):562-570 (2002).
Cho C.Y. et al., "An Unnatural Biopolymer", Science 261:1303-1305 (Sep. 3, 1993).
Cornetta K. et al., "Gene Transfer into Primates and Prospects for Gene Therapy in Humans", Progress in Nucleic Acid Research 36:311-322 (1987).
Cull M.G. et al., "Screening for Receptor Ligands Using Large Libraries of Peptides Linked to the C Terminus of the Lac Repressor", Proc. Natl. Acad. Sci. USA 89:1865-1869 (Mar. 1992).
Cwirla S.E. et al., "Peptides on Phage: A Vast Library of Peptides for Identifying Ligands", Proc. Natl. Acad. Sci. USA 87:6378-6382 (Aug. 1990).

(56) References Cited

OTHER PUBLICATIONS

Devlin J.J. et al., "Random Peptide Libraries: A Source of Specific Protein Binding Molecules", Science 249:404-406 (1990).

Dewitt S.H. et al., ""Diversomers": An Approach to Nonpeptide, Nonoligomeric Chemical Diversity", Proc. Natl. Acad. Sci. USA 90:6909-6913 (Aug. 1993).

Erb E. et al., "Recursive Deconvolution of Combinatorial Chemical Libraries", Proc. Natl. Acad. Sci. USA 91:11422-11426 (Nov. 1994).

Felgner P.L. et al., "Lipofection: A Highly Efficient, Lipid-Mediated DNA-Transfection Procedure", Proc. Natl. Acad. Sci. USA 84:7413-7417 (Nov. 1987).

Felici F., "Selection of Antibody Ligands from a Large Library of Oligopeptides Expressed on a Multivalent Exposition Vector", Mol. Biol. 222:301-310 (1991).

Fernandez-Hernando C. et al., "MicroRNAs in Lipid Metabolism", Curr Opin Lipidol 22:86-95 (2011).

Fodor S.P.A. et al., "Multiplexed Biochemical Assays With Biological Chips", Nature 364:555-556 (Aug. 5, 1993).

Friedewald W.T. et al., "Estimation of the Concentration of Low-Density Lipoprotein Cholesterol in Plasma, Without Use of the Preparative Ultracentrifuge", Clinical Chemistry 18(6):499-502 (1972).

Friedmann T., "Progress Toward Human Gene Therapy", Science 244:1275-1281 (Jun. 16, 1989).

Gallop M.A. et al., "Applications of Combinatorial Technologies to Drug Discovery. 1. Background and Peptide Combinatorial Libraries", Journal of Medicinal Chemistry 37(9):1233-1251 (Apr. 29, 1994).

Gerin I. et al., "Expression of miR-33 from an SREBP2 Intron Inhibits Cholesterol Export and Fatty Acid Oxidation", The Journal of Biological Chemistry 285(44):33652-33661 (Oct. 29, 2010).

Goldberg M.A. et al., "Treatment of Sickle Cell Anemia With Hydroxyurea and Erythropoietin", The New England Journal of Medicine 323:366-372 (Aug. 9, 1990).

Guo H-C et al., "Lipoprotein Lp(a) in Homozygous Familial Hypercholesterolemia: Density Profile, Particle Heterogeneity and Apolipoprotein(a) Phenotype", Atherosclerosis 31:69-83 (1991).

Houghten R.A. et al., "The Use of Synthetic Peptide Combinatorial Libraries for the Identification of Bioactive Peptides", BioTechniques 13(3):412-421 (1992).

Horie T. et al., "MicroRNA-33 Encoded by an Intron of Sterol Regulatory Element-Binding Protein 2 (Srebp2) Regulates HDL In Vivo", PNAS 107(4):17321-17326 (Oct. 5, 2010).

Hussain M.M. et al., "Microsomal Triglyceride Transfer Protein and its Role in apoB-Lipoprotein Assembly", Journal of Lipid Research 44:22-32 (2003).

Hussain M.M. et al., "Microsomal Triglyceride Transfer Protein in Plasma and Cellular Lipid Metabolism", Current Opinion in Lipidology 19:277-284 (2008).

Hussain M.M. et al., "New Approaches to Target Microsomal Triglyceride Transfer Protein", Current Opinion in Lipidology 19:572-578 (2008).

Hussain M.M. et al., "Characterization of Recombinant Human ApoB-48-Containing Lipoproteins in Rat Hepatoma McA-RH7777 Cells Transfected With ApoB-48 cDNA: Overexpression of ApoB-48 Decreases Synthesis of Endogenous ApoB-100", Arteriosclerosis, Thrombosis, and Vascular Biology 15(4):485-494 (Apr. 1995).

Johnson L.G., "Gene Therapy for Cystic Fibrosis", Chest 107(2):77S-83S (Feb. 1995).

Kido M. et al., "Use of a Retroviral With an Internal Opsin Promoter to Direct Gene Expression to Retinal Photoreceptor Cells", Current Eye Research 15:833-844 (1996).

Lam K.S. et al., "A New Type of Synthetic Peptide Library for Identifying Ligand-Binding Activity", Nature 354:82-84 (Nov. 7, 1991).

Le Gal La Salle G. et al., "An Adenovirus Vector for Gene Transfer into Neurons and Glia in the Brain", Science 259:988-990 (Feb. 12, 1993).

Lee R.C. et al., "The C. Elegans Heterochronic Gene Lin-4 Encodes Small RNAs With Antisense Complementarity to Lin-14", Cell 75:843-854 (Dec. 3, 1993).

Manzoni M. et al., "Biosynthesis and Biotechnological Production of Statins by Filamentous Fungi and Application of These Cholesterol-Lowering Drugs", Appl Microbiol Biotechnol 58:555-564 (2002).

Marquart T.J. et al., "MiR-33 Links SREBP-2 Induction to Repression of Sterol Transporters", PNAS 107 (27):12228-12232 (Jul. 6, 2010).

Miller A.D., "Retrovirus Packaging Cells", Human Gene Therapy 1:5-14 (1990).

Miller A.D. et al., "Improved Retroviral Vectors for Gene Transfer and Expression", Biotechniques 7(9):980-990 (Oct. 1989).

Miyoshi H. et al., "Stable and Efficient Gene Transfer into the Retina Using an HIV-Based Lentiviral Vector", Proc. Natl. Acad. Sci. USA 94:10319-10323 (Sep. 1997).

Moen R.C., "Directions in Gene Therapy", Blood Cells 17:407-416 (1991).

Moore K.J. et al., "The Role of MicroRNAs in Cholesterol Efflux and Hepatic Lipid Metabolism", Annu. Rev. Natur. 31:6.1-6.15 (Apr. 25, 2011).

Najafi-Shoushtari S.H. et al., "MicroRNA-33 and the SREBP Host Genes Cooperate to Control Cholesterol Homeostasis", Science 328:1566-1569 (Jun. 18, 2010).

Naldini L. et al., "In Vivo Gene Delivery and Stable Transduction of Nondividing Cells by a Lentiviral Vector", Science 272:263-267 (Apr. 12, 1996).

Ono T. et al., "Plasmid DNAs Directly Injected into Mouse Brain With Lipofectin Can Be Incorporated and Expressed by Brain Cells", Neuroscience Letters 117:259-263 (1990).

Raabe M. et al., "Knockout of the Abetalipoproteinemia Gene in Mice: Reduced Lipoprotein Secretion in Heterozygotes and Embryonic Lethality in Homozygotes", Proc. Natl. Acad. Sci. USA 95:8686-8691 (Jul. 1998).

Rava P. et al., "Transfer of Cholesteryl Esters and Phospholipids as Well as Net Deposition by Microsomal Triglyceride Transfer Protein", Journal of Lipid Research 46:1779-1785 (2005).

Rava P. et al., "Acquisition of Triacylglycerol Transfer Activity by Microsomal Triglyceride Transfer Protein During Evolution", Biochemistry 46:12263-12274 (2007).

Rayner K.J. et al., "MiR-33 Contributes to the Regulation of Cholesterol Homeostasis", Science 328:1570-1573 (Jun. 18, 2010).

Scott J.K. et al., "Searching for Peptide Ligands With an Epitope Library", Science 246:386-390 (1990).

Sharp D., "Gene Therapy", The Lancet 337:1277-1278 (May 25, 1991).

Straubinger R.M. et al., "Liposomes as Carriers for Intracellular Delivery of Nucleic Acids", Methods in Enzymology 101:512-527 (1983).

Tolstoshev P. et al., "Gene Expression Using Retroviral Vectors", Current Opinion in Biotechnology 1:55-61 (1990).

Ventura A. et al., "MicroRNAs and Cancer: Short RNAs Go a Long Way", Cell 136:586-591 (Feb. 20, 2009).

Wetterau J.R. et al., "An MTP Inhibitor That Normalizes Atherogenic Lipoprotein Levels in WHHL Rabbits", Science 282:751-754 (Oct. 23, 1998).

Wetterau J.R. et al., "Absence of Microsomal Triglyceride Transfer Protein in Individuals With Abetalipoproteinemia", Science 258:999-1001 (Nov. 6, 1992).

Wolff J.A. et al., "Direct Gene Transfer into Mouse Muscle In Vivo", Reports 247:1465-1468 (Mar. 23, 1990).

Wu G.Y. et al., "Receptor-Mediated Gene Delivery and Expression In Vivo", The Journal of Biological Chemistry 263 (29):14621-14624 (Oct. 15, 1988).

Wu C.H. et al., "Targeting Genes: Delivery and Persistent Expression of a Foreign Gene Driven by Mammalian Regulatory Elements In Vivo", The Journal of Biological Chemistry 264(29):16985-16987 (Oct. 15, 1989).

Zuckermann R.N. et al., "Discovery of Nanomolar Ligands for 7-Transmembrane G-Protein-Coupled Receptors from a Diverse N-(Substituted)Glycine Peptoid Library", J. Med. Chem. 37:2678-2685 (1994).

(56) References Cited

OTHER PUBLICATIONS

Eglitis M.A. et al., "Retroviral Vectors for Introduction of Genes into Mammalian Cells", BioTechniques 6(7):608-614 (1988).

* cited by examiner

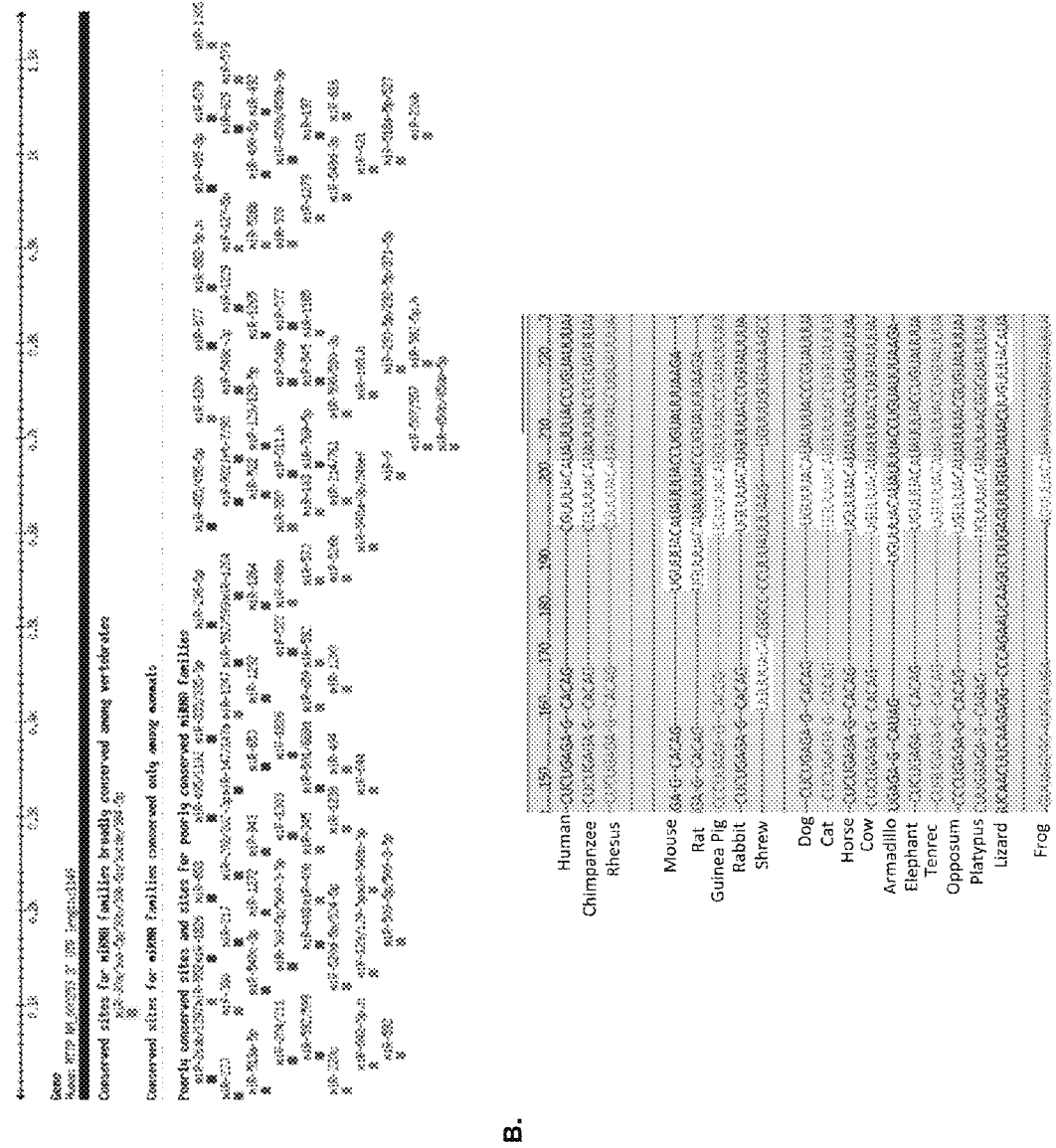
Figure S1

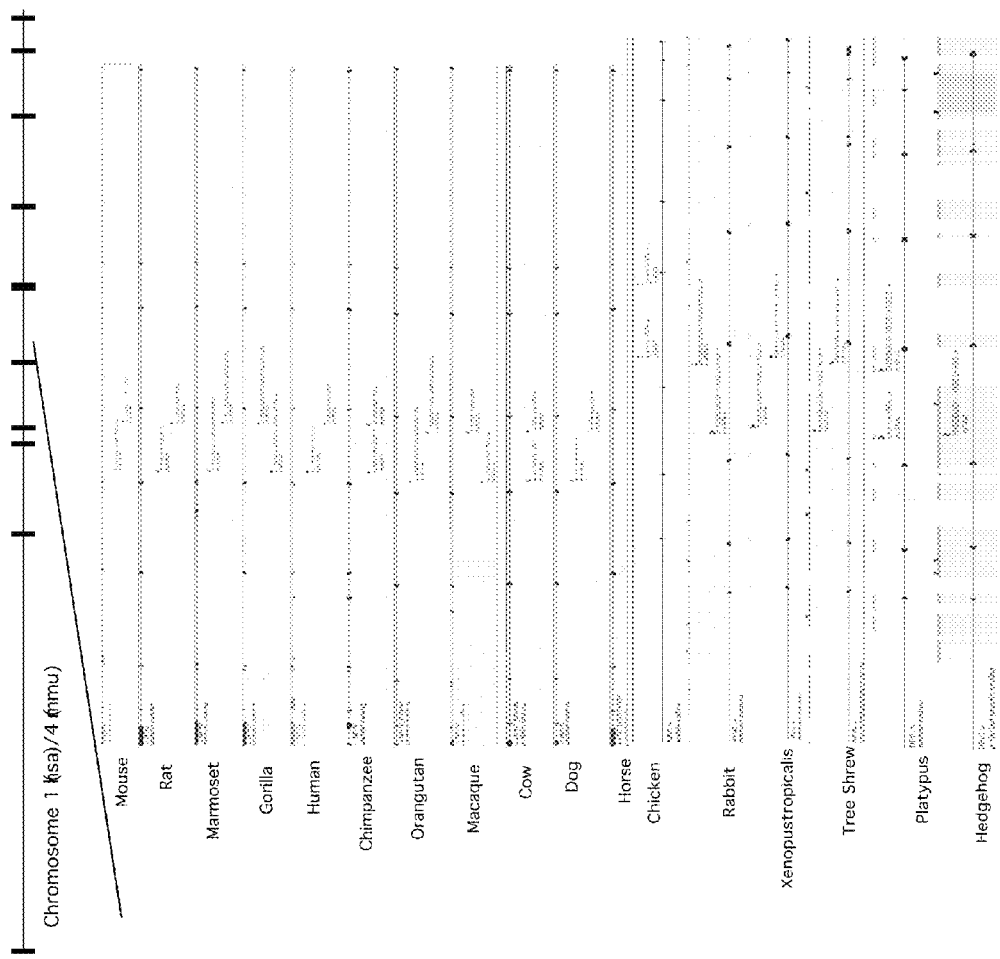
Figure S2

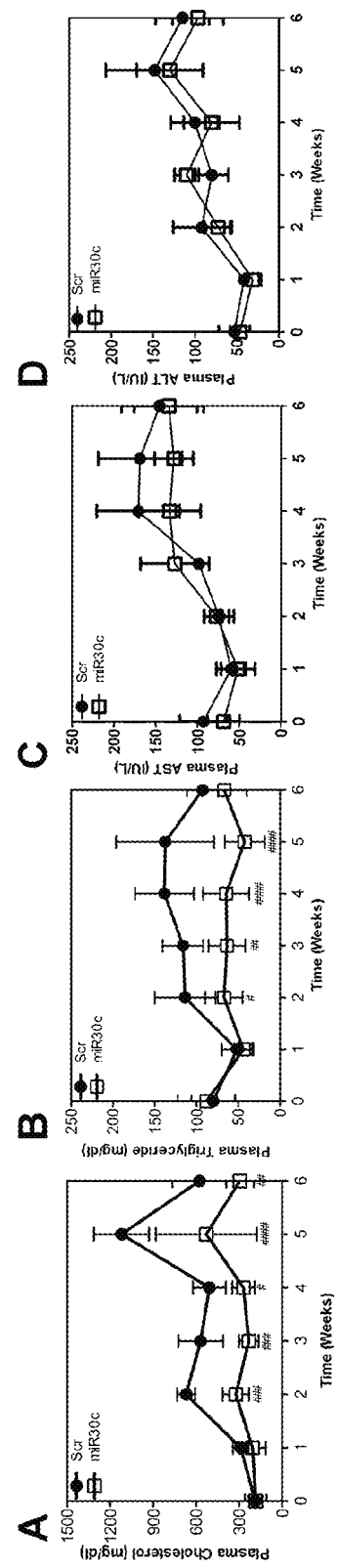
Figure S3

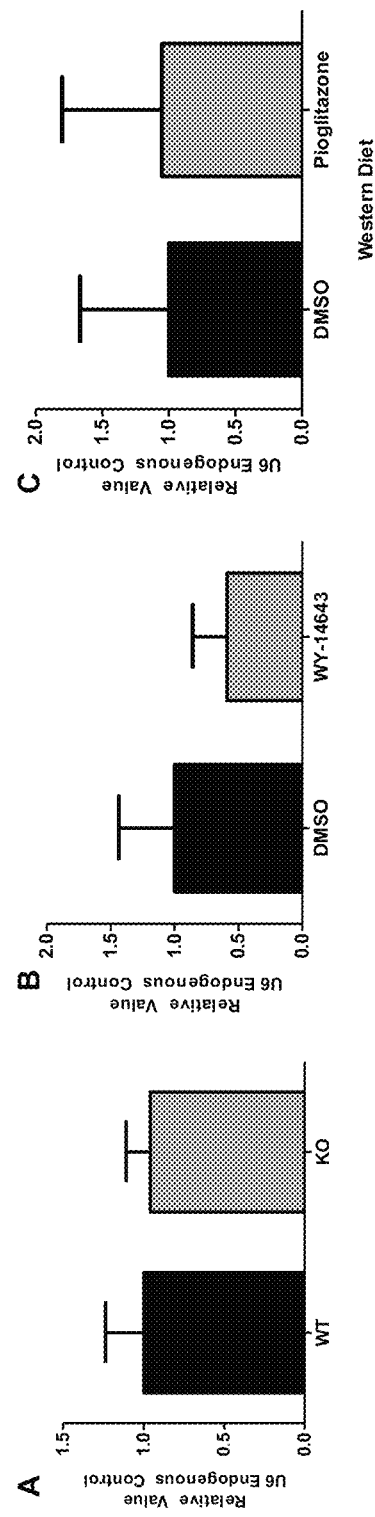
Figure S4

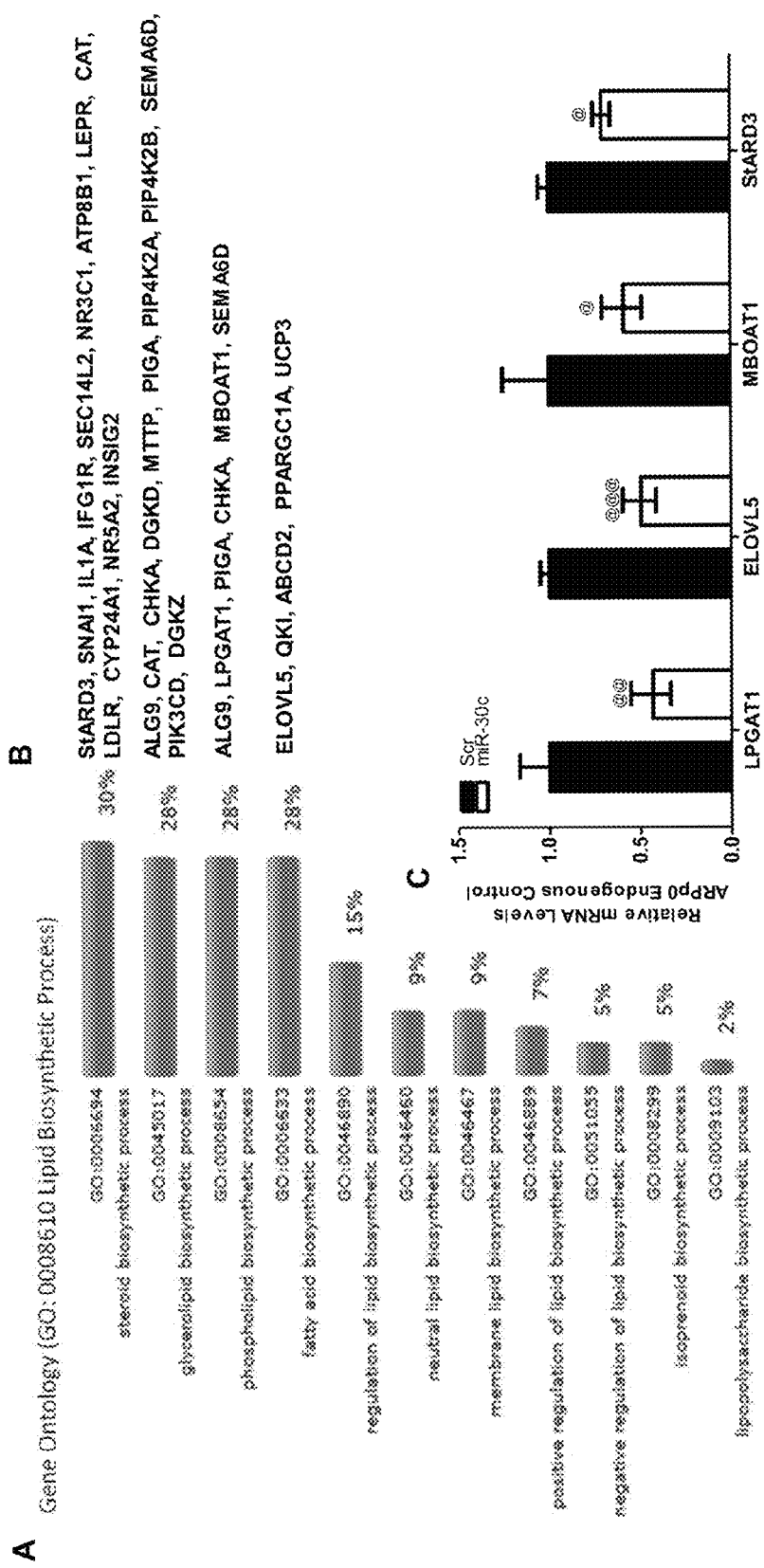
Figure S5

SEQUENCE LISTING

```
<160> NUMBER OF SEQ ID NOS: 2

<210> SEQ ID NO 1
<211> LENGTH: 89
<212> TYPE: RNA
<213> ORGANISM: Artificial Sequence
<220> FEATURE:
<223> OTHER INFORMATION: pre-miR-30c

<400> SEQUENCE: 1
accaugcugu agugugugua aacauccuac acucucagcu gugagcucaa gguggcuggg     60 agagguugu uuacuccuuc ugccaugga                                        89

<210> SEQ ID NO 2
<211> LENGTH: 23
<212> TYPE: RNA
<213> ORGANISM: Artificial Sequence
<220> FEATURE:
<223> OTHER INFORMATION: mature-miR-30c

<400> SEQUENCE: 2
uguaaacauc cuacacucuc agc                                             23
```

METHOD OF TREATING HYPERLIPIDEMIA AND ATHEROSCLEROSIS WITH MIR-30C

CROSS-REFERENCE TO RELATED APPLICATION

This application claims the benefit of priority of U.S. Provisional Application 61/584,958, filed Jan. 10, 2012, the content of which is incorporated herein by reference.

STATEMENT REGARDING FEDERALLY SPONSORED RESEARCH OR DEVELOPMENT

This invention was made with government support under grants DK-46900 and HL-95924 awarded by the National Institutes of Health. The government has certain rights in the invention.

INCORPORATION BY REFERENCE OF SEQUENCE LISTING

The Sequence Listing in the ASCII text file, named as 28080_SequenceListing.txt of 4 KB, created on Dec. 14, 2015, and submitted to the United States Patent and Trademark Office via EFS-Web, is incorporated herein by reference.

BACKGROUND OF THE DISCLOSURE

Complications from excess plasma lipid accumulation are one of the most common causes of death in Western societies (1;2) because they enhance risks for various cardiovascular and metabolic disorders such as hyperlipidemia, atherosclerosis, heart disease, and metabolic syndrome. In plasma, lipids are transported on lipoproteins that provide endogenously produced and dietary lipids to tissues. Plasma lipid levels are controlled by lipoprotein assembly and their catabolism. Hence, reducing lipoprotein production can be a useful approach to prevent and/or treat various cardiovascular and metabolic disorders.

Lipoproteins are synthesized by the intestine and liver using a structural protein, apolipoprotein B (apoB) with the assistance of microsomal triglyceride transfer protein (MTP) (3;4). The assembly of apoB-containing lipoproteins requires two steps. The first step occurs within the endoplasmic reticulum that involves the synthesis of particles that contain only a small fraction of the lipid core found in the secreted lipoprotein. A larger core of lipid is added to the nascent particle in a second step. MTP is considered essential for the transfer of various lipids to apoB during the first step of the process.

Pharmacologic inhibition of MTP with Bristol-Myers Squibb's BMS-201038, a potent chemical inhibitor of MTP, reduced low density lipoprotein cholesterol (LDL-C) in volunteers with hypercholesterolemia. However, steatorrhea, elevation of serum transaminases and hepatic fat accumulation were observed. Thus, Bristol-Myers Squibb decided that these side effects made it unlikely that BMS-201038 could be developed as a drug for large scale use in the treatment of hypercholesterolemia. Combinations using MTP inhibitors and other cholesterol or triglyceride drugs have been previously disclosed (U.S. Pat. Nos. 6,066,653 and 5,883,109) but suffer the same drawbacks as described above for MTP inhibitors used alone. Thus, novel approaches are needed to harness beneficial effects of reduced MTP activity.

Hypercholesterolemia is a well-known risk factor for atherosclerotic cardiovascular disease (ASCVD), the major cause of mortality in the Western world. Numerous epidemiological studies have clearly demonstrated that pharmacological lowering of total cholesterol (TC) and Low-density Lipoprotein (LDL) Cholesterol (LDL-C) is associated with a significant reduction in clinical cardiovascular events. Hypercholesterolemia is often caused by a polygenic disorder in the majority of cases and modifications in lifestyle and conventional drug treatment are usually successful in reducing cholesterol levels. However, in few cases, as in familial hypercholesterolemia, the cause is a monogenic defect and the available treatment in homozygous patients can be much more challenging and far from optimal because LDL-C levels remain extremely elevated despite aggressive use of combination therapy. Therefore, for this group of high-risk patients, effective medical therapy is urgently needed.

Triglycerides are common types of fats (lipids) that are essential for good health when present in normal amounts. They account for about 95 percent of the body's fatty tissue. Abnormally high triglyceride levels can result from such causes as cirrhosis of the liver, underactive thyroid (hypothyroidism), poorly controlled diabetes, or pancreatitis (inflammation of the pancreas). Researchers have also identified elevated triglycerides as a risk factor for heart disease.

Higher-than-normal triglyceride levels are often associated with known risk factors for heart disease, such as low levels of HDL ("good") cholesterol, high levels of LDL ("bad") cholesterol and obesity. Triglycerides may also contribute to thickening of artery walls, which is linked to the development of atherosclerosis.

MicroRNAs (miRs) are small noncoding RNA molecules that can cause post-transcriptional silencing of specific genes, either by the inhibition of translation or through degradation of the targeted mRNA. Since the initial discovery of miRs as regulators of gene expression (11), a role of miRs in development of various diseases such as cancer (12) has been identified. MiRs interact with the 3'-untranslated region (3'-UTR) of target mRNAs and reduce protein synthesis by enhancing mRNA degradation and/or by interfering with its translation (13). A microRNA can be completely complementary or can have a region of noncomplementarity with a target nucleic acid, consequently resulting in a "bulge" at the region of non-complementarity.

Two miRs have been shown to be involved in lipid metabolism miR-122 is linked to fatty acid synthesis and oxidation and is currently being tested as a therapeutic target against hepatitis C infection (1) miR-33 regulates expression of ABCA1 and ABCG1, two proteins involved in reverse cholesterol transport (14-18).

A further understanding of the regulation of lipid metabolism by miRs can reveal new physiological mechanisms to reduce lipoprotein production, hyperlipidemia and atherosclerosis.

BRIEF SUMMARY OF THE DISCLOSURE

This disclosure provides a novel role for microRNA (miR) regulation of lipid metabolism via the MTP pathway, leading to reductions in apoB secretion and blood lipid levels. MiR regulation of the MTP pathway is shown herein to reduce hyperlipidemia and atherosclerosis in vivo. Therefore, inhibition of MTP expression and activity by miR regulation is identified as a new therapeutic target for treatment of cardiovascular disease and conditions or diseases associated with cardiovascular disease such as hyperlipidemia, atherosclerosis, and metabolic syndrome.

In one embodiment, this disclosure provides a method for treating cardiovascular disease, hyperlipidemia, atherosclerosis, or metabolic syndrome in a subject in need thereof, comprising administration of a miR-30c homolog or agonist in an amount effective to treat the disease in said subject. A particular embodiment further provides administration of the miR-30c homolog or agonist in combination with at least one additional cholesterol reducing agent, such as a statin.

In another embodiment, this disclosure provides a method for reducing serum lipids in a subject in need thereof, comprising administration of a miR-30c homolog or agonist in an amount effective to reduce serum lipids in said subject. A particular embodiment further provides administration of the miR-30c homolog or agonist in combination with at least one additional cholesterol reducing agent, such as a statin.

In an additional embodiment, this disclosure provides a method for reducing MTP activity in a subject in need thereof, comprising administration of a miR-30c homolog or agonist in an amount effective to reduce MTP activity in said subject.

In another embodiment, this disclosure provides a pharmaceutical composition for the treatment of cardiovascular disease, hyperlipidemia, atherosclerosis, or metabolic syndrome, comprising an effective amount of a miR-30c homolog or agonist.

In a further embodiment, this disclosure provides a method of identifying an agent for the treatment of cardiovascular disease, hyperlipidemia, atherosclerosis, obesity, diabetes, Hepatitis C infection, or metabolic syndrome, comprising contacting a cell expressing a miR-30c homolog with a candidate agent, and assaying the expression of the miR-30c homolog; wherein an increase in expression of the miR-30c homolog identifies the agent as a miR-30c homolog agonist useful for the treatment of cardiovascular disease, hyperlipidemia, atherosclerosis, or metabolic syndrome.

In another embodiment, this disclosure provides a method of reducing lipid synthesis in a subject in need thereof, comprising administration of a miR-30c homolog or agonist in an amount effective to reduce lipid synthesis in said subject.

Another embodiment provides a method of coordinately suppressing lipid synthesis and lipid secretion by the liver to lower plasma lipids while avoiding build up of lipids in the liver by administering an effective dose of miR-30c homolog or agonist in said subject.

Figure 1:
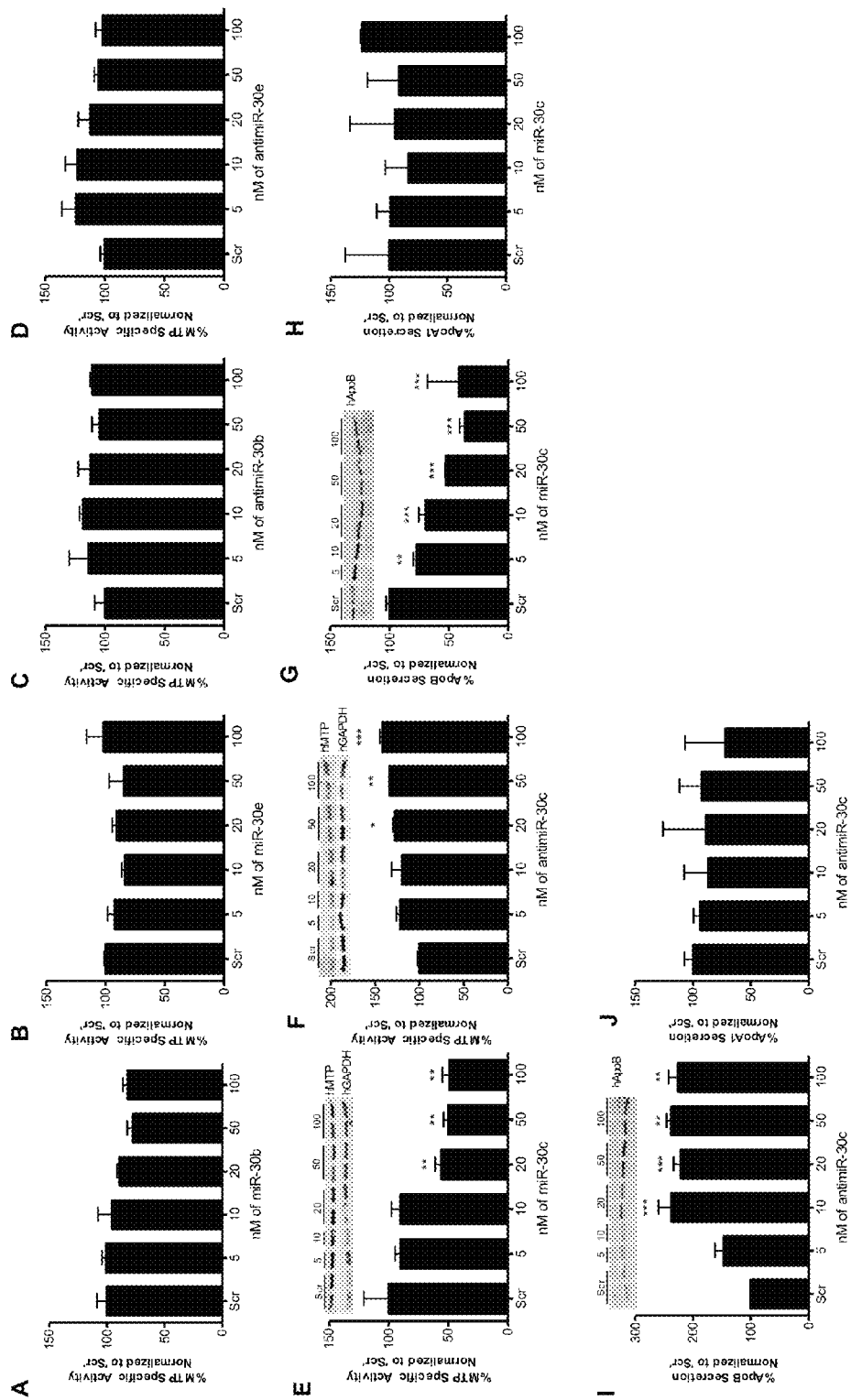
FIG. 1: Effect of different miR-30s and anti-miR-30s on MTP activity and protein. Huh-7 cells were transfected in triplicate with different amounts of miR-30b (A), miR-30e (B), anti-miR-30b (C), antagomiR-30e (D), miR-30c (E), anti-miR-30c (F) or a non-specific Scramble miR (Scr) at 100 nM. After 48 hr, cells were used for MTP activity (Bars) and protein (insets) measurements. Media were used to quantify apoB (G, I) and apoAI (H, J). Data are representative of multiple experiments.

FIG. S1: miR-30 binding to MTP: (A) TargetScan was used to search for miRs that could interact with the 3'-untranslated region (UTR) of human MTP mRNA. This search reveals possible binding of several miRs to the MTP transcripts. Next, conservation of the binding sites in various mammalian MTP 3'-UTR was determined. These studies revealed that vertebrate MTP mRNAs contain conserved binding sites for the several members of the miR-30 family (a, a-5p, b, b-5p, c, d, and e) and miR-384-5p. (B) This figure shows putative binding sites for miR-30c in different vertebrate MTP mRNA. Pairing site for miR-30c in the 3'-UTR of various mammalian MTP sequences are highlighted in white.

FIG. S2. Conservation of miR-30c in vertebrates: Top line shows schematic representation of different introns and exons in the human NFY-C gene miR-30c and miR-30e reside in intron 5 of the gene. Their location is highly conserved in vertebrates.

FIG. S3. Effect of miR-30c and antimiR-30c on plasma lipids and atherosclerosis: Female Apoe$^{-/-}$ mice (n=7/group) were injected with lentiviruses expressing miR-30c or Scr miR and started on a Western diet. Plasma cholesterol (A), triglyceride (B), AST (C) and ALT (D) were measured weekly. # $p<0.05$; ## $p<0.01$, ### $p<0.001$, #### $p<0.0001$; significance calculated by two-way ANOVA.

FIG. S4. miR-30c is not regulated by common MTP regulators: (A) miR-30c expression was assessed by qRT-PCR in the livers of MTP$^{flox/flox}$ and MTP liver-specific knockout mice. (B) C57/B16 wild type mice were treated with WY-14643 compound, a known PPAR-alpha agonist by oral gavage. DMSO was used as a control. (n=4/group) (C) C57/B16 wild-type mice were fed a high fat diet and simultaneously treated with pioglitazone, a known agonist for PPAR-gamma. DMSO was used as a control. (n=5/group)

FIG. S5: Lipid biosynthesis processes are targeted by miR-30c: (A) Predicted target genes of miR-30c from TargetScan were used to identify pathways affected using Gene Ontology. This program identified several lipid biosynthetic processes to be targeted by miR-30c. (B) Different genes targeted by miR-30c in various processes are listed. (C) Huh-7 cells were transfected in triplicate with Scr or miR-30c. After 48 h, mRNAs were isolated to quantify candidate genes and ARPp0 (endogenous control). Ratios in Scr cells were normalized to 1. @ $p<0.05$; @@ $p<0.01$, @@@ $p<0.001$, @@@@ $p<0.0001$; significance calculated by student t-test.

DETAILED DESCRIPTION OF THE DISCLOSURE

In the following description, reference is made to the accompanying drawings that form a part hereof, and in which is shown by way of illustration specific embodiments that can be practiced. These embodiments are described in detail to enable those skilled in the art to practice the invention, and it is to be understood that other embodiments can be utilized and that logical changes can be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

This disclosure provides a novel role for microRNA (miR) regulation of lipid metabolism via the regulation of lipid synthesis and lipoprotein secretion pathways, leading to reductions in apoB secretion and blood lipid levels while avoiding accumulation of lipids in the liver. MiR regulation of the lipid synthesis and lipoprotein secretion pathway is shown herein to reduce hyperlipidemia and atherosclerosis in vivo. The lipid secretion pathway is affected by reductions in MTP expression whereas reductions in lipid synthesis involve several genes such as LPGAT1, ELOVL5, MBOAT1. Therefore, inhibition of MTP expression and activity by miR as well as coordinate down regulation of lipid synthesis is identified as a new therapeutic target for treatment of cardiovascular disease and conditions or diseases associated with cardiovascular disease such as hyperlipidemia, atherosclerosis, and metabolic syndrome. Treatment of cardiovascular disease and associated conditions or diseases with the novel inhibitors of the invention, such as miR-30c homologs or miR-30c agonists, reduces MTP-associated lipid production as well as lipid synthesis via other pathways without side effects that occur with other methods of treatment and MTP inhibition.

MTP and Lipid Metabolism.

Microsomal triglyceride transfer protein (MTP) catalyzes the transport of triglyceride, cholesteryl ester, and phosphatidylcholine onto lipoprotein carriers. MTP interacts with lipids and apoB to transfer lipids to apoB during the assembly of apoB-containing lipoproteins. In the absence of MTP-mediated lipid transfer, apoB-containing lipoproteins are not produced, and lipid transport in the blood is reduced. Thus, inhibition of MTP lowers serum lipids.

As used herein, the term "lipid" or "lipids" refers to lipid molecules of any type, including fatty acids or acyls such as eicosanoids; glycerolipids such as fats/triglycerides; glycerophospholipids such as phosphatidylcholine; sphingolipids such as ceramides; sterol lipids such as cholesterol; prenol lipids such as quinines; saccarolipids; and polyketides.

Inhibition of MTP with Reduced Side Effects.

Although reduction of lipoprotein production and transport is desirable for treatment of elevated blood lipid levels, treatment with previously developed MTP inhibitors resulted in undesirable side effects such as elevated serum transaminases, hepatic fat accumulation, and steatorrhea, the presence of excess fat in the stools causing chronic diarrhea. These side effects suggest possible liver damage as well as intestinal malfunction with the use of other MTP inhibitors. Therefore, an important aspect of the invention is the inhibition of MTP and reduction of serum lipid levels without these side effects, or where these side effects are reduced relative to previously reported levels of such side effects using other MTP inhibitors. This is possible because the MTP inhibitors of the invention are herein shown to be efficacious in vivo in reducing MTP expression and serum lipid levels without causing liver damage.

"Inhibition" or "reduction" as described herein includes, for example, a 5%, 10%, 25%, 50%, 75%, 80%, 90%, 95%, or even 100% reduction. In some embodiments, MTP activity or expression is reduced or inhibited by 10%, 20%, 25%, 30%, 40%, 50%, 60%, 70%, 75%, 80%, 85%, 90%, 95%, or 100% compared to MTP activity or expression in an untreated or control subject. Methods for testing for reduction/inhibition of MTP activity or expression are known to those of skill in the art and are set forth, for example, in U.S. Pat. No. 5,789,197. In some embodiments, MTP expression is reduced or inhibited by miR binding to the MTP mRNA. In other embodiments, serum or plasma lipid levels in a subject are reduced 5%, 10%, 15%, 20%, 25%, 30%, 35%, 40%, 45%, 50%, 55%, or 60% or more following treatment with the methods and compositions of the invention, compared to lipid levels in the same subject prior to treatment with the methods and compositions of the invention.

The MTP inhibitors of the invention reduce MTP expression and activity without negatively affecting liver health or elevating serum transaminases. Liver health and serum transaminase levels can be determined, for example, by measuring levels of aspartate transaminase (AST or SGOT) and/or alanine transaminase (ALT or SGPT). AST and ALT are commonly measured clinically as a part of diagnostic liver function tests, to determine liver health. Normal AST ranges=8-40 IU/L (men), 6-34 IU/L (women). 5-60 U/L is considered a normal range for ALT, although levels fluctuate over the day for any given individual. The MTP inhibitors of the invention are shown in the Examples below to reduce MTP activity and expression without negatively affecting, for example, AST/ALT levels.

The inventors have discovered that MTP can be inhibited by miR regulation of MTP mRNA. This leads to reduction in lipid transfer onto apoB, reduced serum cholesterol and lipids, and reduction in atherosclerotic plaque formation, without unwanted side effects of other inhibitors of MTP.

MTP Inhibitors of the Invention.

The MTP inhibitors of the invention encompass microRNA (miR) regulators of MTP expression and activity, and miR agonists that increase miR expression and activity. As used herein, "inhibiting MTP expression" refers to causing a reduction in MTP protein levels. MTP protein levels may be reduced by reducing transcription of MTP mRNA or pre-mRNA from the MTP gene, such as by preventing binding of a transcription factor to the MTP genomic locus. MTP protein levels may also be reduced by reducing translation of MTP mRNA into MTP protein, such as by preventing binding of a ribozyme to the MTP mRNA, or by increasing the degradation of MTP mRNA or removal of MTP mRNA from the nucleus. As used herein, "inhibiting MTP activity" refers to causing a reduction in at least one MTP activity including, but not limited to, binding lipids, binding apoB, catalyzing transfer of lipids to apoB, facilitating lipoprotein production, increasing apoB lipoprotein secretion, increasing serum lipid levels, and increasing serum cholesterol and triglyceride levels.

The term "microRNA" or "miR" refers to a microRNA molecule found in eukaryotes that is involved in RNA-based gene regulation. MiRs interact with the 3'-untranslated region (3'-UTR) of target mRNAs and can reduce protein synthesis by enhancing target gene mRNA degradation and/or by interfering with target gene translation (13). A microRNA according to the invention can be 18-100 nucleotides in length, and more preferably from 18-80 nucleotides in length. Mature or active miRs can have a length of 19-30 nucleotides, preferably 21-25 nucleotides, particularly 21, 22, 23, 24, or 25 nucleotides. The invention also can include double-stranded precursors of miRs MiR precursors typically have a length of about 70-100 nucleotides and have a hairpin conformation. MiRs are generated in vivo from miR precursors by the enzymes Dicer and Drosha, which specifically process long pre-miRNA into functional miRNA. A microRNA can be completely complementary to the target sequence of the target mRNA or can have a region of noncomplementarity with a target mRNA, consequently resulting in a "bulge" at the region of non-complementarity.

The active nucleotide miR molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that active and precursor miR molecules can also be produced directly by biological or chemical synthesis by methods known in the art. When a microRNA is referred to herein by name, the name corresponds to both the precursor and mature forms, unless otherwise indicated.

This invention provides miRs useful for inhibiting expression or activity of MTP. In a particular embodiment, the miR is a miR-30c homolog. By "miR-30c homolog" is meant a nucleic acid molecule that binds the 3' UTR of microsomal triglyceride transfer protein (MTP) mRNA, where such nucleic acid molecule has a nucleobase sequence with at least 75%, 80%, 85%, 90%, 95%, 97%, 99% or 100% identity to the sequence of miR-30c, miR-Base Accession #:MI0000736, or a fragment or derivative thereof. Exemplary miR-30c sequences follow:

TABLE-1

```
pre-miR-30c sequence:
ACCAUGCUGUAGUGUGUGUAAACAUCCUACACUCUCAGCUGUGAGCUCA
AGGUGGCUGGGAGAGGGUUGUUUACUCCUUCUGCCAUGGA
(SEQ. ID NO: 1) (hairpin) and mature sequence:
UGUAAACAUCCUACACUCUCAGC (SEQ ID NO: 2).

MTP binding domain/seed sequence: 5'-UGUAAAC-3'.
```

By "miR-30c gene" is meant a polynucleotide that encodes a miR-30c homolog, or analog thereof. By "oligonucleotide" is meant any molecule comprising a nucleobase sequence. An oligonucleotide may, for example, include one or more modified bases, linkages, sugar moieties, or other modifications. By "fragment" is meant a portion of a miR molecule. This portion contains, preferably, at least 10%, 20%, 30%, 40%, 50%, 60%, 70%, 80%, or 90% of the entire length of the miR nucleic acid molecule. A fragment may contain 5, 6, 7, 8, 9, 10, 11, 12, 13, 14, 15, 16, 17, 18, 19, 20, or 21 or more nucleotides. By "derivative" is meant a nucleic acid that comprises sufficient sequence to bind to and inhibit MTP mRNA.

miR-30c activities include binding to MTP mRNA or the MTP mRNA 3' UTR, increasing MTP mRNA degradation, inhibiting MTP expression and/or activity, reducing lipoprotein production, reducing plasma cholesterol levels, reducing plasma triglyceride levels, reducing lipids in plasma VLDL fraction, reducing or preventing hyperlipidemia, reducing or preventing obesity, reducing or preventing diabetes, reducing or preventing atherosclerosis, reducing or preventing atherosclerotic plaque formation, reducing or preventing metabolic syndrome, preventing or reducing Hepatitis C virus infection, and other viral infections that require apoB-lipoproteins for their propagation.

If desired, miR-30c homologs may be modified to stabilize the microRNA against degradation, to enhance half-life, or to otherwise improve efficacy. Desirable modifications are described, for example, in U.S. Patent Publication Nos. 20070213292, 20060287260, 20060035254, 20060008822, and 20050288244, each of which is hereby incorporated by reference in its entirety.

For increased nuclease resistance and/or binding affinity to the target, the miR-30c homolog can include 2'-O-methyl, 2'-fluorine, 2'-O-methoxyethyl, 2'-O-aminopropyl, 2'-amino, and/or phosphorothioate linkages. Inclusion of locked nucleic acids (LNA), ethylene nucleic acids (ENA), e.g., 2'-4'-ethylene-bridged nucleic acids, and certain nucleobase modifications can also increase binding affinity to the target. The inclusion of pyranose sugars in the oligonucleotide backbone can also decrease endonucleolytic cleavage. An agent can be further modified by including a 3' cationic group, or by inverting the nucleoside at the 3'-terminus with a 3'-3' linkage. In another alternative, the 3'-terminus can be blocked with an aminoalkyl group. Other 3' conjugates can inhibit 3'-5' exonucleolytic cleavage. While not being bound by theory, a 3' may inhibit exonucleolytic cleavage by sterically blocking the exonuclease from binding to the 3' end of the oligonucleotide. Even small alkyl chains, aryl groups, or heterocyclic conjugates or modified sugars (D-ribose, deoxyribose, glucose etc.) can block 3'-5'-exonucleases. It is understood that the methods and reagents of the present invention may be used in conjunction with any technologies that may be developed to enhance the stability or efficacy of an inhibitory nucleic acid molecule.

miR-30c homologs include nucleobase oligomers containing modified backbones or non-natural internucleoside linkages. Oligomers having modified backbones include those that retain a phosphorus atom in the backbone and those that do not have a phosphorus atom in the backbone. United States patents that teach the preparation of phosphorus-containing linkages include, but are not limited to, U.S. Pat. Nos. 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

miR-30c homolog nucleobase oligomers having modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. United States patents that teach the preparation of the above oligonucleotides include, but are not limited to, U.S. Pat. Nos. 5,470,967; 5,489,677; 5,541, 307; 5,561,225; 5,596,086; 5,602,240; 5,608,046; 5,610, 289; 5,618,704; 5,623,070; 5,633,360; and 5,677,439, each of which is herein incorporated by reference.

miR-30c homolog nucleobase oligomers may also contain one or more substituted sugar moieties. United States patents that teach the preparation of such modified sugar structures include, but are not limited to, U.S. Pat. Nos. 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

This disclosure further provides miR-30c agonists to inhibit MTP expression and/or activity. A "miR-30c agonist" is an agent that increases miR-30c activity. An agent that increases miR-30c activity may, for example, increase the expression of miR-30c, augment miR-30c activity, or prevent miR-30e inhibition or degradation.

This disclosure further provides nucleic acids encoding a miR-30c homolog, such as the miR-30c gene, or miR-30c agonist, for administration to a subject in need of treatment according to the methods of the invention.

Treatment of Diseases.

This disclosure provides methods for treating cardiovascular disease, hyperlipidemia, atherosclerosis, metabolic syndrome, and related diseases and conditions in a subject in need thereof, comprising administration of a miR-30c homolog or agonist in an amount effective to treat the disease in said subject.

Further, this disclosure provides methods for reducing serum lipids in a subject in need thereof, comprising administration of a miR-30c homolog or agonist in an amount effective to reduce serum lipids in said subject.

Additionally, this disclosure provides methods for reducing MTP activity in a subject in need thereof, comprising administration of miR-30c or a miR-30c homolog or agonist in an amount effective to reduce MTP activity in the subject.

The terms "treat," "treating," or "treatment" as used herein with regards to a condition refers to slowing the onset or rate of development of the condition, delaying the development of symptoms associated with the condition, reducing or ending symptoms associated with the condition, generating a complete or partial regression of the condition, or some combination thereof. For example, with regard to atherosclerosis, "treatment" can refer to a decrease in the rate of development of atherosclerotic plaque deposits, a decrease in the number or size of existing deposits, or improved plaque stability. Likewise, "treatment" with regard to hyperlipidemia can refer to a decrease in lipid levels, cholesterol levels, and/or triglyceride (TG) levels in blood, serum, or plasma in a treated subject relative to levels in said subject prior to treatment. Similarly, "treatment" with regard to cardiovascular disease can refer to an increase in HDL/LDL ratio, or a decrease in blood pressure or hypertension.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The subject who is in need of treatment with a miR-30c homolog or agonist can be any animal, including a human. The subject is generally diagnosed with the condition by skilled artisans, such as a medical practitioner. The methods of the invention described herein can be employed for subjects of any species, gender, age, ethnic population, or genotype.

The therapeutic methods of the invention include administration of an effective amount of the agents herein, such as a miR-30c homolog or a miR-30c agonist or a nucleic acid encoding such a miR-30c homolog or a miR-30c agonist to a subject in need thereof.

The term "effective amount," as used herein, refers to the amount necessary to elicit the desired biological response. In accordance with the subject invention, the effective amount of a miR-30c homolog or agonist is the amount necessary to provide an observable effect in at least one biological factor (i.e., observable decrease in MTP/ApoB levels) for use in treating a biological condition (such as lowering total blood cholesterol levels in a patient diagnosed with hypercholesterolemia). The effective amount can include the amount necessary to enable a 1%-85% decrease in total serum cholesterol or lipid levels. In certain embodiments, the effective amount enables a 5%, 10%, 20%, 25%, 30%, 35%, 40%, 45%, 50%, 55%, 60%, 65%, 70%, 75%, 80%, 85%, 90%, 95%, 98%, 99% and 100% decrease in severity of complications associated with the biological condition (i.e., complications related to cardiovascular disease or hypercholesterolemia such as obesity, heart disease, stroke, hypertension, etc.).

Accordingly, the present invention provides methods of treating disease and/or disorders or symptoms thereof which comprise administering an effective amount of a miR-30c homolog or a miR-30c agonist as described herein to a subject. Thus, one embodiment is a method of treating a subject suffering from or susceptible to a lipid-related disorder, or symptom thereof. The method includes the step of administering to the subject an effective amount of a miR-30c homolog or a miR-30c agonist or nucleic acid encoding such a miR-30c homolog or a miR-30c agonist herein sufficient to treat the lipid-related disease or disorder or symptom thereof, under conditions such that the disease or disorder is treated.

The methods herein include administering to the subject an effective amount of a compound described herein, or a composition described herein to prevent, treat, stabilize, or reduce plasma lipid levels in a subject in need thereof. Identifying a subject in need of such treatment can be in the judgment of a subject or a health care professional and can be subjective (e.g. opinion) or objective (e.g. measurable by a test or diagnostic method).

Conditions Treatable.

Biological conditions that can be treated via the administration of a miR-30c homolog or a miR-30c agonist as disclosed herein include, but are not limited to, hypercholesterolemia; high triglyceride levels (including high LDL levels); obesity, cardiovascular disease; metabolic syndrome; hypertension; diabetes; as well as any other symptoms, complications, conditions, or diseases associated with these diseases. In accordance with the subject invention, the administration of miR-30c homolog or a miR-30c agonist to a patient can delay or prevent the development of such biological conditions and any associated symptoms, complications, conditions, or diseases associated with said biological condition.

As used herein, the phrase "disorders associated with hyperlipidemia and/or hypercholesterolemia" refers to diseases and disorders related to or caused by elevated lipid or cholesterol levels. Such diseases and disorders include, without limitation, hypercholesterolemia, severe hypercholesterolemia, familial combined hyperlipidemia, familial hypercholesterolemia, remnant hyperlipidemia, chylomicronemia syndrome and familial hypertriglyceridemia. In some embodiments, the disease is severe hypercholesterolemia. In some embodiments, the disease is homozygous/heterozygous familial hypercholesterolemia. In some embodiments the disease is hypertriglyceridemia or hyperlipidemia. In some embodiments the disease is familial combined hyperlipidemia. In some embodiments disease is viral infections.

As used herein, the term "hyperlipidemia" refers to a pathognomic condition manifest by elevated serum concentrations of total cholesterol (>200 mg/dL), LDL cholesterol (>130 mg/dL), or triglycerides (>150 mg/dL) or decreased HDL cholesterol (<40 mg/dL). Further, as used herein, "triglycerides" refers to triacylglycerol esters of fatty acids.

The term "cholesterol level" as used herein refers to blood cholesterol level, serum cholesterol level, plasma cholesterol level, or cholesterol level from another biological fluid. A decrease in cholesterol levels as used herein may refer to a decrease in total cholesterol levels or a decrease in one or more of total cholesterol, non-HDL cholesterol, LDL, VLDL, and/or IDL levels. A decrease in LDL as used herein may refer to a decrease in total LDL, a decrease in LDL particles, a decrease in small LDL particles, a decrease in oxidized LDL levels, and/or a decrease in ApoB levels. A decrease in VLDL as used herein may refer to a decrease in total VLDL or to a decrease in the level of one or more of VLDL subparticles V1 to V6. An improvement in HDL/LDL ratio as used herein refers to any increase in the ratio of HDL to LDL, and may be accomplished by decreasing LDL levels, increasing HDL levels, or some combination thereof. An increase in LDL particle size as used herein refers to an increase in mean particle size.

The term "elevated cholesterol level" as used herein refers to a cholesterol level that is above an accepted normal threshold level, such as those promulgated by the National Heart Lung and Blood Institute (NHLBI). The accepted normal threshold cholesterol level may vary from subject to subject based on various risk factors, such as for example a prior history of cardiovascular disease (CVD). In certain embodiments, a subject exhibiting elevated cholesterol levels may have a blood LDL level greater than or equal to 70 mg/dl. In certain of these embodiments, a subject exhibiting elevated cholesterol levels may have a blood LDL greater than or equal to 100 mg/dl, in other embodiments greater than or equal to 130 mg/dl, in other embodiments greater than or equal to 160 mg/dl, and in still other embodiments greater than or equal to 190 mg/dl. In certain embodiments, a subject exhibiting elevated cholesterol levels may have a blood total cholesterol level greater than or equal to 200 mg/dl. In certain of these embodiments, a subject exhibiting elevated cholesterol levels may have blood total cholesterol greater than or equal to 240 mg/dl.

The term "triglyceride level" as used herein refers to blood triglyceride level, serum triglyceride level, plasma triglyceride level, or triglyceride level from another biological fluid. The term "elevated triglyceride level" as used herein refers to a triglyceride level that is above an accepted normal threshold level. The accepted normal threshold triglyceride level may vary from subject to subject based on various risk factors, such as for example a prior history of CVD. In certain embodiments, a subject exhibiting elevated triglyceride levels may have a blood triglyceride level greater than or equal to 150 mg/dl. In certain of these embodiments, a subject exhibiting elevated triglyceride levels may have a blood triglyceride level greater than or equal to 200 mg/dl, in other embodiments greater than or equal to 300 mg/dl, in other embodiments greater than or equal to 400 mg/dl, and in still other embodiments greater than or equal to 500 mg/dl.

The present invention provides methods for the treatment and/or prevention of elevated lipids, or for preventing, delaying, and/or treating the development of elevated lipid-related complications.

In one embodiment, the subject invention provides materials and methods for treating and/or preventing high cholesterol or hypercholesterolemia, or for preventing, delaying, and/or treating the development of hypercholesterolemia (or high cholesterol)-related complications, through the administration of a miR-30c homolog or agonist to a subject in an amount effective to reduce MTP activity. In another embodiment is provided materials and methods for treating and/or preventing high plasma lipids or hyperlipidemia, or for preventing, delaying, and/or treating the development of hyperlipidemia (or high plasma lipid)-related complications, through the administration of a miR-30c homolog or agonist to a subject in an amount effective to reduce MTP activity.

In some embodiments, one or more of total cholesterol levels, plasma LDL-cholesterol levels, triglyceride levels, fasting triglycerides (TG) levels, VLDL levels, lipoprotein (a) (Lp(a)) levels, or Apolipoproteins A-I, A-II, B, and E levels in the subject are reduced by at least 15%, by at least 25%, at least 30%, at least 40%, at least 50%, at least 60%, at least 70%, at least 75%, or at least 80% compared to control blood levels.

In some embodiments, triglyceride levels achieved are less than 500 mg/dl. In some embodiments, triglyceride levels achieved are less than 300 mg/dl. In some embodiments, triglyceride levels achieved are less than 200 mg/dl. In some embodiments, triglyceride levels achieved are less than 150 mg/dl.

In some embodiments, the ApoB/ApoA1 ratio achieved by treatment according to the present invention is from 0.25 to 1.25. In some embodiments the ApoB/ApoA1 ratio achieved is from 0.1 to 2.0. In some embodiments the apoB level achieved is from 48-130. In some embodiments the apoB level achieved is from 20-180.

As used herein, a "control blood level" refers to a level of a particular blood component in the absence of treatment according to the present invention. In some embodiments, the "control blood level" is the level of a particular blood component in the subject prior to treatment of the subject according to the present invention. In some embodiments, the "control blood level" is the level of a particular blood component if a subject either receiving a placebo or receiving a different treatment; e.g. a treatment not including at least three step-wise, increasing dosages of an MTP inhibitor. Reduction of levels of blood components, including, for example, cholesterol, triglycerides, and apolipoprotein B, can be determined by comparing pre-treatment levels to levels during or after treatment according to the present invention.

Methods of measuring levels of particular components of blood are well-known to those of skill in the art. For example, total plasma cholesterol and triglyceride concentrations may be determined by a modification of the Liebermann-Burchard reaction (Abell L L, Levy B B, Brodie B B, Kendall F E. A simplified method for the estimation of total cholesterol in serum and demonstration of its specificity. J Biol Chem. 1952; 195:357-362) and by the method of Kessler and Lederer after zeolite extraction, (Kessler G, Lederer H. Fluorometric measurement of triglycerides. In: Skeggs L T, Jr, eds. Automation in Analytical Chemistry: Technicom Symposia. New York, N.Y.: Madiad Inc; 1965: 341-344), respectively. Plasma HDL cholesterol may be estimated by the method of Allain et al (Allain C C, Poon L S, Chan G S G, Richmond W, Fu P C. Enzymatic determination of total serum cholesterol. Clin Chem. 1974; 20:470-475) using an enzymatic kit (Biotrol). LDL cholesterol may be calculated using the Freidewald formula. (Freidewald W T, Levy R I, Fredrickson D S. Estimation of the concentration of low density lipoprotein-cholesterol in plasma without the use of the preparative ultracentrifuge. Clin Chem. 1972; 18:499-502). Plasma apoB, apoAI, and lipoprotein(a) levels may be measured by immunological assays as described earlier (Guo H, Chapman M J, Bruckert E, Farriaux J P, De Gennes J L. Lipoprotein Lp(a) in homozygous familial hypercholesterolemia: density profile, particle heterogeneity and apolipoprotein(a) phenotype. Atherosclerosis. 1991; 31:69-83) and based on laser immunonephelometry (Immuno AG).

"Cardiovascular disease" (CVD) as used herein includes, for example, atherosclerosis, coronary artery disease (CAD), coronary heart disease (CHD), conditions associated with CAD and CHD, cerebrovascular disease and conditions associated with cerebrovascular disease, peripheral vascular disease and conditions associated with peripheral vascular disease, aneurysm, vasculitis, venous thrombosis, and metabolic syndrome. "Conditions associated with CAD and CHD" as used herein include, for example, angina and myocardial infarction (heart attack). "Conditions associated with cerebrovascular disease" as used herein include, for example, transient ischemic attack and stroke. "Conditions associated with peripheral vascular disease" as used herein include, for example, claudication. "Conditions associated with CVD" as used herein include, for example, low HDL/LDL ratio, and hypertension. Treatment of cardiovascular disease includes treatment of any one or more of the diseases and conditions as described in this paragraph.

"Arteriosclerosis" or "atherosclerosis" as used herein refers to a disease state characterized by the development and growth of atherosclerotic lesions or plaque. The identification of those patients who are in need of treatment for atherosclerosis is well within the knowledge and ability of one skilled in the art. For example, patients who are either suffering from clinically significant atherosclerosis or who are at risk of developing atherosclerosis as a result of hypercholesterolemia are considered patients in need of treatment for a complication associated with hypercholesterolemina.

Over time, hypercholesterolemia and hypertriglyceridemia can lead to the development of atheromatous plaques on the inner arterial linings via the process of atherogenesis, which in turn results in atherosclerosis. Atherosclerosis leads to significantly reduced blood flow through the arteries, which in turn leads to the development of CAD, CHD, and conditions associated with CAD and CHD.

Thus, in a further embodiment is provided materials and methods for treating and/or preventing atherosclerosis, or for preventing, delaying, and/or treating the development of atherosclerosis or atherosclerosis-related complications, through the administration of an effective amount of a miR-30c homolog or agonist to a subject in need thereof. In a further embodiment is provided materials and methods for treating and/or preventing cardiovascular disease, or for preventing, delaying, and/or treating the development of cardiovascular disease or cardiovascular disease-related complications, through the administration of an effective amount of a miR-30c homolog or agonist to a subject in need thereof.

People with metabolic syndrome are at increased risk of coronary heart disease and other diseases related to plaque buildup in artery walls (e.g., stroke and peripheral vascular disease) and type 2 diabetes. Metabolic syndrome has become increasingly common in the United States and worldwide. It is estimated that over 50 million Americans have risk factors indicating metabolic syndrome. The dominant underlying risk factors for this syndrome appear to be abdominal obesity and insulin resistance. Other conditions associated with the syndrome include physical inactivity, aging, hormonal imbalance and genetic predisposition.

Metabolic syndrome is a disorder characterized by a group of metabolic risk factors. These factors include, for example, dyslipidemia, abdominal obesity, elevated blood pressure (hypertension), insulin resistance or glucose intolerance, prothrombotic state, and proinflammatory state. Subjects are generally classified as having metabolic syndrome if they meet three of the five following criteria: 1) abdominal obesity (waist circumference >35 inches in women, >40 inches in men); 2) low HDL levels (<50 mg/dL in women, <40 mg/dL in men); 3) high blood pressure (equal to or greater than 130/85 mm Hg) or current treatment with antihypertensive medication; 4) hypertriglyceridemia (TG levels equal to or greater than 150 mg/dL); and 5) impaired fasting glucose (blood glucose levels equal to or greater than 100 mg/dL). Treatment of metabolic disease includes a reduction in at least one of these criteria as defined herein.

Administration.

One exemplary approach provided by the invention involves administration of a therapeutic miR-30c homolog or agonist, either directly to the site of a potential or actual disease-affected tissue or systemically (for example, by any conventional administration technique). The dosage of the administered miR-30c homolog or agonist depends on a number of factors, including the size and health of the individual patient. For any particular subject, the specific dosage regimes should be adjusted over time according to the individual need and the professional judgment of the person administering or supervising the administration of the compositions.

A miR-30c homolog of the invention, which may be in the mature or hairpin form, may be provided as a naked oligonucleotide that is capable of entering a cell. In some cases, it may be desirable to utilize a formulation that aids in the delivery of the miR-30c homolog to cells (see, e.g., U.S. Pat. Nos. 5,656,611, 5,753,613, 5,785,992, 6,120,798, 6,221,959, 6,346,613, and 6,353,055, each of which is hereby incorporated by reference).

In some examples, the miR-30c homolog or agonist composition is at least partially crystalline, uniformly crystalline, and/or anhydrous (e.g., less than 80, 50, 30, 20, or 10% water). In another example, the miR-30c homolog or agonist composition is in an aqueous phase, e.g., in a solution that includes water. The aqueous phase or the crystalline compositions can be incorporated into a delivery vehicle, e.g., a liposome (particularly for the aqueous phase), or a particle (e.g., a microparticle as can be appropriate for a crystalline composition). Generally, the miR-30c homolog or agonist composition is formulated in a manner that is compatible with the intended method of administration.

A miR-30c homolog or agonist composition can be formulated in combination with another agent, e.g., another therapeutic agent or an agent that stabilizes an oligonucleotide agent, e.g., a protein that complexes with the oligonucleotide agent. Still other agents include chelators, e.g., EDTA (e.g., to remove divalent cations such as Mg.sup.2+), salts, and RNAse inhibitors (e.g., a broad specificity RNAse inhibitor, such as RNAsin).

Polynucleotide therapy featuring a polynucleotide encoding a miR-30c homolog or agonist is another therapeutic approach. Expression vectors encoding the microRNAs can be delivered to cells of a subject, such as hepatic cells, for inhibition of MTP in the liver. The nucleic acid molecules must be delivered to the cells of a subject in a form in which they can be taken up and are advantageously expressed so that therapeutically effective levels can be achieved.

Methods for delivery of the polynucleotides to the cell according to the invention include using a delivery system, such as liposomes, polymers, microspheres, gene therapy vectors, and naked DNA vectors.

Transducing viral (e.g., retroviral, adenoviral, lentiviral and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a polynucleotide encoding a miR-30c homolog or agonist can be cloned into a retroviral vector and expression can be driven from its endogenous promoter, from the retroviral long terminal repeat, or from a promoter specific for a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, The Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7:980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med 323:370, 1990; Anderson et al., U.S. Pat. No. 5,399,346).

Non-viral approaches can also be employed for the introduction of a miR-30c homolog to a patient. For example, a miR-30c homolog or agonist can be introduced into a cell by administering the nucleic acid in the presence of lipofection (Feigner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., Journal of Biological Chemistry 263:14621, 1988; Wu et al., Journal of Biological Chemistry 264:16985, 1989), or by micro-injection under surgical conditions (Wolff et al., Science 247:1465, 1990).

miR-30c homolog or agonist expression for use in polynucleotide therapy methods can be directed from any suitable promoter (e.g., the human cytomegalovirus (CMV), simian virus 40 (SV40), or metallothionein promoters), and regulated by any appropriate mammalian regulatory element. For example, if desired, enhancers known to preferentially direct gene expression in specific cell types can be used to direct the expression of a nucleic acid. The enhancers used can include, without limitation, those that are characterized as tissue- or cell-specific enhancers.

In order to realize the therapeutic effect of MTP inhibition, the miR-30c homolog or agonist is administered in an effective amount, also referred to herein as a "therapeutically-effective" amount. As is well known in the art, the dosage of the active ingredient(s) significantly depends on such factors as the method of administration, size of the subject, and potential side effects. In different embodiments, depending on these and other factors, a suitable dosage of the active ingredient of the miR-30c homolog or agonist, or miR-30c homolog or agonist composition, can be precisely, at least, or no more than, for example, 1 mg, 10 mg, 50 mg, 100 mg, 200 mg, 300 mg, 400 mg, 500 mg, 600 mg, 700 mg, 800 mg, 900 mg, 1000 mg, 1200 mg, or 1500 mg, or a dosage within a range bounded by any of the foregoing exemplary dosages. Further to the above embodiments, depending on the same and other factors, the composition is administered in the indicated amount by any suitable schedule, e.g., once, twice, or three times a day for a total treatment time of one, two, three, four, or five days, and up to, for example, one, two, three, or four weeks. Alternatively, or in addition, the treatment is administered until a desired amount of MTP inhibition is reached. The desired level of MTP inhibition can be any level deemed by a professional in the medical arts to be appropriate to achieve, and can be measured directly, by measuring levels of MTP, or indirectly, by measuring improvement in one or more symptoms experienced by the subject in need of treatment.

Generally, doses of active polynucleotide compositions of the present invention would be from about 0.01 mg/kg per day to about 1000 mg/kg per day. It is expected that doses ranging from about 50 to about 2000 mg/kg will be suitable. Lower doses will result from certain forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of the miR-30c homolog or agonist of the invention or of a polynucleotide encoding such a miR-30c homolog or agonist.

For any particular subject, the specific dosage regimes should be adjusted over time according to the individual need and the professional judgment of the person administering or supervising the administration of the compositions.

Pharmaceutical Compositions.

This disclosure provides therapeutic compositions containing a miR-30c homolog or agonist as described herein for the treatment or prevention of lipid-associated conditions. In one embodiment, the present invention provides a pharmaceutical composition for the treatment of cardiovascular disease, hyperlipidemia, atherosclerosis, or metabolic syndrome, comprising an effective amount of a miR-30c homolog or agonist. In another embodiment is provided a pharmaceutical composition comprising a miR-30c homolog or agonist or a nucleic acid molecule encoding a miR-30c homolog or agonist. In another embodiment, a miR-30c homolog or agonist or a polynucleotide encoding such a miR-30c homolog or agonist, is administered to reduce MTP activity. Polynucleotides of the invention may be administered as part of a pharmaceutical composition. The compositions should be sterile and contain a therapeutically effective amount of a miR-30c homolog or agonist or nucleic acid molecule encoding a miR-30c homolog or agonist in a unit of weight or volume suitable for administration to a subject.

A miR-30c homolog or agonist or a nucleic acid molecule encoding a miR-30c homolog or agonist described herein may be administered within a pharmaceutically-acceptable diluent, carrier, or excipient, in unit dosage form. Conventional pharmaceutical practice may be employed to provide suitable formulations or compositions to administer the compounds to patients suffering from a lipid-associated condition. Administration may begin before the patient is symptomatic. Any appropriate route of administration may be employed, for example, administration may be parenteral, intravenous, intraarterial, subcutaneous, intratumoral, intramuscular, intracranial, intraorbital, ophthalmic, intraventricular, intrahepatic, intracapsular, intrathecal, intracisternal, intraperitoneal, intranasal, aerosol, suppository, or oral administration. For example, therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" Ed. A. R. Gennaro, Lippincourt Williams & Wilkins, Philadelphia, Pa., 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for inhibitory nucleic acid molecules include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The formulations can be administered to human patients in therapeutically effective amounts depending on such variables as the type and extent of the disorder, the overall health status of the particular patient, the formulation of the compound excipients, and its route of administration.

Combination Therapy—

The compositions herein are further provided in combination with one or more additional therapeutic means to treat cardiovascular disease, hyperlipidemia, atherosclerosis, or metabolic syndrome, for example by reducing plasma lipid and cholesterol levels, and/or reducing or reversing atherosclerotic plaque formation.

Reducing Fat and Cholesterol Intake.

This disclosure provides for administration of an effective amount of the compositions of the invention in combination with a reduced fat, reduced cholesterol diet. The primary means of reducing or eliminating dietary cholesterol and lipid intake occurs through changes in food intake. Total dietary cholesterol is preferably limited to below 200 mg per day, even more preferably below 100 mg per day. A patient is assigned a diet in which high-fat and high-cholesterol foods (such as egg yolks, high fat dairy products such as whole milk, organ meats, and pastries) and saturated fats are to be significantly reduced, and are preferably eliminated entirely. Saturated fatty acids are precursors for cholesterol synthesis and therefore, the level of their intake is positively associated with higher cholesterol level. Major food sources of saturated fat are animal food-based products (bacon, lard, butter, etc.) and fried foods.

It is recommended that the patient substitute unsaturated fats for saturated fats. Replacement of foods high in saturated fatty acids with polyunsaturated or monounsaturated fat rich foods reduces serum cholesterol levels. Unsaturated fat includes polyunsaturated fat and monounsaturated fat, both of which are predominantly found in plant products. Examples of polyunsaturated fat food sources include soybean, sunflower, fish and corn oils. Monounsaturated fat is found in high content in olive, peanut, and canola oils.

High fiber foods such as unprocessed whole grains, vegetables, and fruits, are encouraged. Foods rich in fiber, both soluble and insoluble fiber, prevent the re-absorption of cholesterol-rich bile acids from the small intestines back into circulation, thereby reducing circulating cholesterol. Thus, high-fiber, unprocessed foods inhibit cholesterol absorption and lower cholesterol in the body. The patient may also consume fiber supplements, such as Metamucil™ or Benefiber™, to increase dietary fiber intake.

Food containing phytosterols are further encouraged. Phytosterols are sterol compounds produced by plants which, because they are structurally very similar to cholesterol, inhibit cholesterol uptake in the digestive system Important sources of phytosterols are rice bran, corn bran, corn germ, wheat germ oil, corn oil, safflower oil, olive oil, cotton seed oil, soybean oil, e.g., soybean oil distillates, peanut oil, black tea, orange juice, green tea, kale, broccoli, sesame seeds, shea oils, grapeseed oil, rapeseed oil, linseed oil, and canola oil.

Prevention of dietary cholesterol absorption in the intestines may be augmented by treating the patient with a cholesterol absorption inhibitor (CAI). CAIs include, for example, ezetimibe; 1,4-Diphenylazetidin-2-ones; 4-biarylyl-1-phenylazetidin-2-ones; 4-(hydroxyphenyl)azetidin-2-ones; 1,4-diphenyl-3-hydroxyalkyl-2-azetidinones; 4-biphenyl-1-phenylazetidin-2-ones; 4-biarylyl-1-phenylazetidin-2-ones; and 4-biphenylylazetidinones. Another class of CAIs are bile acid sequestrants, such as cholestyramine, colesevelam and colestipol.

Blocking De Novo Cholesterol Synthesis.

This disclosure further provides for administration of an effective amount of the compositions of the invention in combination with at least one additional cholesterol reducing agent. Such agents reduce serum cholesterol by partially or completely blocking de novo cholesterol synthesis. Cholesterol reducing agents encompass several classes of drugs that include HMG CoA reductase inhibitors (statins), γ-tocotrienol, bisphosphonates, cholesterol-ester-transfer-protein ("CETP") inhibitors, squalene synthase inhibitors, soluble guanylate cyclase modulators ("sGC modulators"), nicotinic acid, and derivatives thereof (e.g. AGI-1067). In a preferred embodiment, the cholesterol reducing agent is a statin.

Statins, γ-tocotrienol, and bisphosphonates inhibit the mevalonate to cholesterol conversion pathway. Statins and γ-tocotrienol inhibit HMG-CoA reductase, a rate-limiting enzyme necessary for cholesterol production, and decrease the production of mevalonate and subsequent products on the way to construction of the cholesterol molecule. Statin therapy has been demonstrated to provide significant reductions in serum cholesterol levels. For example, administration of atorvastatin 80 mg daily significantly lowers plasma cholesterol concentrations. Statins include, but are not limited to, atorvastatin (Lipitor®), bervastatin, carvastatin, crilvastatin, dalvastatin, fluvastatin (Lescol®), glenvastatin, fluindostatin, velostatin, lovastatin (mevinolin; Mevacor®), pravastatin (Pravachol®), rosuvastatin (Crestor®), and simvastatin (Zocor®). Statins identical to lovastatin and its derivatives can be produced by a variety of filamentous fungi, including *Monascus, Aspergillus, Penicillium, Pleurotus, Pythium, Hypomyces, Paecilomyces, Eupenicillium*, and *Doratomyces* (Manzoni M, Rollini M., *Appl Microbiol Biotechnol*. 58:555-64, 2002).

Bisphosphonates (such as clodronate and etidronate) that closely resemble pyrophosphate—a normal byproduct of human metabolism—are incorporated into adenosine triphosphate (ATP) analogues. The newest generation of bisphosphonates, which contain nitrogen (such as pamidronate, alendronate, risedronate, and ibandronate), are believed to inhibit post-translational modification within the mevalonate pathway.

A cholesterol reducing agent can be orally administered in the form of a sublingual tablet, buccal tablet, extended-release (long-acting) capsule, or spray. For a statin, about 2 mg to 80 mg, about 5 mg to 40 mg, or about 10 to 80 mg of a statin per day for an adult can be orally administered. For a cholesterol absorption inhibitor (e.g. ezetimibe), about 2 mg to 80 mg, about 5 mg to 40 mg, or about 10 to 80 mg of a cholesterol absorption inhibitor per day for an adult can be orally administered. For a bile acid sequestrant (e.g. cholestyramine, colesevelam or colestipol), about 1 g to 30 g, about 0.2 g to 6 g, about 0.1 g to 3 g, about 0.02 g to 0.6 g, about 0.01 g to 0.3 g, about 5 g to 150 g, about 2 g to 60 g or about 10 g to 300 g of a bile acid sequestrant per day for an adult can be orally administered.

This disclosure further provides kits for the treatment or prevention of cardiovascular disease, hyperlipidemia, atherosclerosis, or metabolic syndrome. In one embodiment, the kit provides a miR-30c homolog or agonist, or a nucleotide encoding a miR-30c homolog or agonist, for administration to a subject. The kit can also be useful in evaluating efficacies in cell culture and animal models.

Screening Assays.

This disclosure further provides a method of identifying an agent for the treatment of cardiovascular disease, hyperlipidemia, atherosclerosis, or metabolic syndrome, the method involving contacting a cell expressing a miR-30c homolog with a candidate agent; and assaying the expression of a miR-30c homolog, where an increase in the a miR-30c homolog expression identifies the agent as a miR-30c homolog agonist useful for the treatment of cardiovascular disease, hyperlipidemia, atherosclerosis, or metabolic syndrome.

One embodiment of the invention encompasses a method of identifying an agent that increases the expression or activity of a miR-30c homolog. Accordingly, compounds that increase the expression or activity of a microRNA of the invention or a variant, or portion thereof are useful in the methods of the invention for the treatment or prevention of cardiovascular disease, hyperlipidemia, atherosclerosis, or metabolic syndrome. Any number of methods are available for carrying out screening assays to identify such compounds. In one approach, the method comprises contacting a cell that expresses miR-30c with an agent and comparing the level of expression in the cell contacted by the agent with the level of expression in a control cell, wherein an agent that increases the expression of a microRNA of the invention thereby inhibits MTP and is identified as an agent for the treatment or prevention of cardiovascular disease, hyperlipidemia, atherosclerosis, or metabolic syndrome.

In other embodiments, the agent acts as a microRNA mimetic, which substantially fulfills the function of an microRNA of the invention. Candidate mimetics include organic molecules, peptides, polypeptides, nucleic acid molecules. Small molecules of the invention preferably have a molecular weight below 2,000 daltons, more preferably between 300 and 1,000 daltons, and still more preferably between 400 and 700 daltons. It is preferred that these small molecules are organic molecules. Compounds isolated by any approach described herein may be used as therapeutics to treat cardiovascular disease, hyperlipidemia, atherosclerosis, or metabolic syndrome.

Compounds that increase the expression of a microRNA of the invention are also useful in the methods of the invention. Any number of methods are available for carrying out screening assays to identify new candidate compounds that increase the expression of miR-30c. The invention also includes novel compounds identified by the above-described screening assays. Optionally, such compounds are characterized in one or more appropriate animal models to determine the efficacy of the compound for the treatment of cardiovascular disease, hyperlipidemia, atherosclerosis, or metabolic syndrome. Desirably, characterization in an animal model can also be used to determine the toxicity, side effects, or mechanism of action of treatment with such a compound. Furthermore, novel compounds identified in any of the above-described screening assays may be used for the treatment of cardiovascular disease, hyperlipidemia, atherosclerosis, or metabolic syndrome in a subject. Such compounds are useful alone or in combination with other conventional therapies known in the art.

Test Compounds and Extracts.

In general, compounds capable of treating cardiovascular disease, hyperlipidemia, atherosclerosis, or metabolic syndrome by increasing the expression or biological activity of a miR-30c homolog are identified from large libraries of either natural product or synthetic (or semi-synthetic) extracts or chemical libraries according to methods known in the art. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.).

In one embodiment, test compounds of the invention are present in any combinatorial library known in the art, including: biological libraries; peptide libraries (libraries of molecules having the functionalities of peptides, but with a novel, non-peptide backbone which are resistant to enzymatic degradation but which nevertheless remain bioactive; see, e.g., Zuckermann, R. N. et al., J. Med. Chem. 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, Anticancer Drug Des. 12:145, 1997).

Examples of methods for the synthesis of molecular libraries can be found in the art, for example in: DeWitt et al., Proc. Natl. Acad. Sci. U.S.A. 90:6909, 1993; Erb et al., Proc. Natl. Acad. Sci. USA 91:11422, 1994; Zuckermann et al., J. Med. Chem. 37:2678, 1994; Cho et al., Science 261:1303, 1993; Carrell et al., Angew. Chem. Int. Ed. Engl. 33:2059, 1994; Carell et al., Angew. Chem. Int. Ed. Engl. 33:2061, 1994; and Gallop et al., J. Med. Chem. 37:1233, 1994.

Libraries of compounds may be presented in solution (e.g., Houghten, Biotechniques 13:412-421, 1992), or on beads (Lam, Nature 354:82-84, 1991), chips (Fodor, Nature 364:555-556, 1993), bacteria (Ladner, U.S. Pat. No. 5,223,409), spores (Ladner, U.S. Pat. No. 5,223,409), plasmids (Cull et al., Proc Natl Acad Sci USA 89:1865-1869, 1992) or on phage (Scott and Smith, Science 249:386-390, 1990; Devlin, Science 249:404-406, 1990; Cwirla et al. Proc. Natl. Acad. Sci. 87:6378-6382, 1990; Felici, J. Mol. Biol. 222: 301-310, 1991; Ladner supra.). In an embodiment of the invention, a high thoroughput approach can be used to screen different chemicals for their potency to enhance the activity of miR-30c.

Those skilled in the field of drug discovery and development will understand that the precise source of a compound or test extract is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds.

When a crude extract is found to enhance the biological activity of miR-30c, variant, or fragment thereof, further fractionation of the positive lead extract is necessary to isolate chemical constituents responsible for the observed effect. Thus, the goal of the extraction, fractionation, and purification process is the careful characterization and identification of a chemical entity within the crude extract having miR-30c agonistic or MTP-inhibiting activity. Methods of fractionation and purification of such heterogeneous extracts are known in the art. If desired, compounds shown to be useful miR-30c agonists and/or MTP inhibitors are chemically modified according to methods known in the art.

The present description is further illustrated by the following examples, which should not be construed as limiting in any way. The contents of all cited references (including literature references, issued patents, published patent applications as cited throughout this application) are hereby expressly incorporated by reference.

EXAMPLES

Identification of MTP Regulation by miR-30c

Figure 2:
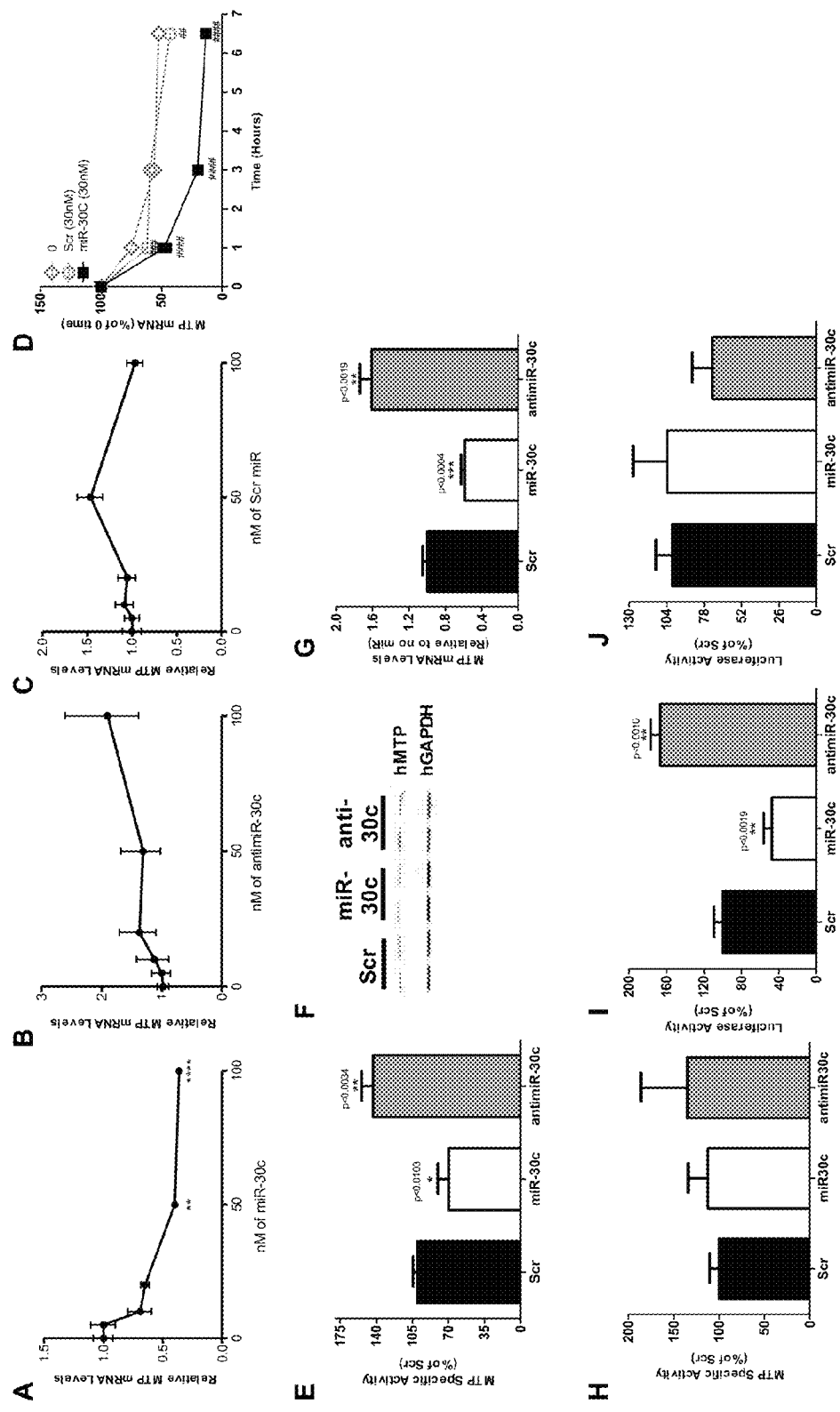
FIG. 2: Regulation of MTP mRNA by miR-30c. (A-C) Huh-7 cells were transfected with different amounts of miR-30c (A), anti-miR-30c (B), or Scr (C). MTP mRNA levels were quantified by qRT-PCR and normalized to ARPp0. Values in cells exposed to no miR were normalized to 1 and values in other cells are reported relative to this value. (D) Huh-7 cells were transfected with indicated miRs After 16 hr, cells were incubated with actinomycin D (10 µg/ml) for different times. MTP/ARPp0 mRNA ratio at 0 hr was normalized to 100%. (E-G) COS-7 cells were transfected with 1.5 µg of pRc-hMTP in 100 mm tissue culture dishes, a plasmid that expresses human MTP using CMV promoter. After overnight incubation, cells were distributed into different wells of 6-well plates and transfected with Scr, miR-30c [30 nM], or anti-miR-30c [30 nM]. After 17 hr, cells were harvested to measure MTP specific activity (E), protein (F), and mRNA (G). Binding of miR-30c to 3'-UTR is necessary for MTP mRNA degradation. MTP sequence in the 3'-UTR was mutated (from GTTTACA in wild type to GAAAACA) in pRc-hMTP and transfected in COS-7 cells. After 17 h, cells were split into different wells and transfected with Scr miR [50 nM], miR-30c [20 nM], or anti-miR-30c [50 nM] and cells were assayed for (H) MTP activity after 17 hr. (I-J) Normal (I) or mutated (J) 3'-UTR sequences of MTP were cloned after the stop codon of Renilla luciferase in psiCHECK2 plasmid that also expresses firefly luciferase and this plasmid was introduced into COS-7 cells. After overnight incubations, cells were transferred to different wells and transfected with Scr [50 nM], miR-30c [20 nM], or anti-miR-30c [50 nM]. Luciferase activities were assayed after 16 h. Ratios of firefly and Renilla luciferase activities were normalized to 100% in cells transfected with Scr.

TargetScan algorithm based on seed recognition identified several miRs that interact with the human MTP transcript. Evolutionary conservation studies among vertebrates, however, narrowed this list to several members of the miR-30 family (FIG. S1A). The miR-30 seed recognition site is conserved in different mammalian MTP mRNAs (FIG. S1B). To examine effects on MTP expression, these miRs were introduced into human hepatoma Huh-7 cells that express MTP and secrete apoB. miR-30b (FIG. 1A), miR-30e (FIG. 1B), antagomiR (anti-miR)-30b (FIG. 1C) and anti-miR-30e (FIG. 1D) had no significant effect on MTP specific activity. Similarly a nonspecific scramble miR (Scr) had no effect compared to no miR (FIG. 1). But miR-30c significantly decreased (~50%) MTP activity and protein levels (FIG. 1E). In particular, miR-30c decreases MTP activity by approximately 50%. MicroRNA-30c mimic (obtained from Dharmacon) was overexpressed in Huh-7 hepatoma cells and incubated for approximately 48 hours. Afterward, MTP activity was assayed using a kit from Chylos, Inc. Effect of MTP activity was compared to a scramble miR that was also transfected in Huh-7 cells in parallel. Further, a miR-30c chemical antagonist, anti-miR-30c, modestly increased MTP protein and activity at higher concentrations compared with Scr (FIG. 2F). This suggested that miR-30c reduces MTP expression, although the modest increase seen with anti-miR-30c suggests that this antagonist is not a potent MTP inducer.

Regulation of MTP and apoB Synthesis by miR-30c is Independent of apoAI.

Since MTP is a critical chaperone for the biosynthesis of apoB-lipoproteins, the inventors studied the effect of miR-30c on apoB secretion in Huh-7 cells. Increasing concentrations of miR-30c decreased apoB (FIG. 1G), but not apoAI (FIG. 1H), secretion. Anti-miR-30c [100 nM] increased apoB secretion by 6- to 10-fold (FIG. 1I) but had no effect on apoAI secretion (FIG. 1J). Scr miR had no effect on apoB and apoAI secretion. These studies indicate that miR-30c reduces MTP expression and apoB-lipoprotein secretion without affecting apoAI secretion.

miR-30c Reduces MTP Protein and Activity by Targeting MTP mRNA.

To understand how miR-30c regulates MTP protein and activity, the inventors measured mRNA levels in cells transfected with miR-30c and anti-miR-30c. Increasing concentrations of miR-30c decreased MTP mRNA by 60-70% (FIG. 2A); however, different concentrations of anti-miR-30c (FIG. 2B) and Scr miR (FIG. 2C) had no significant effect. The absence of specific effect with anti-miR-30c might be related to low expression of miR-30c in these cells. These studies indicated that miR-30c acts by decreasing MTP mRNA.

miR-30c Reduces MTP RNA by Increasing the Rate of MTP RNA Degradation.

Attempts were then made to understand how miR-30c reduces MTP mRNA. Cells were treated with actinomycin D to inhibit gene transcription and studied time dependent changes in MTP mRNA (FIG. 2D). The inventors observed that MTP mRNA was removed faster in cells expressing miR-30c than those expressing either Scr, anti-miR-30c or no miR Mechanisms of MTP mRNA regulation by miR-30c were further evaluated in COS-7 cells that do not express MTP. MTP activity (FIG. 2E), protein (FIG. 2F) and mRNA (FIG. 2G) were reduced when MTP expression plasmids were co-transfected with miR-30c compared to Scr. In contrast, anti-miR-30c increased MTP expression. Thus, miR-30c reduces MTP RNA by increasing the rate of MTP RNA degradation.

miR-30c Binds to the 3'-UTR of MTP mRNA to Induce MTP mRNA Degradation.

Next, the inventors tested the hypothesis that seed sequences in the 3'-UTR of MTP are necessary for mRNA degradation by miR-30c. The miR-30c target sequence is located between 89-95 bases from the stop codon of the human MTP mRNA. The inventors found that miR-30c and its binding site in the 3'-UTR of MTP are conserved in vertebrates (FIG. S1B). This relationship suggests that miR-30c and MTP might have co-evolved and this conservation serves an important function. Mutagenesis of the seed sequence in the 3'-UTR of human MTP abolished miR-30c dependent decrease in MTP activity (FIG. 2H). The importance of 3'-UTR was further evaluated using a psiCHECK2 plasmid encoding a luciferase gene with the 3'-UTR of MTP (FIG. 2I-J). In the presence of miR-30c, the luciferase activity decreased compared to the Scr miR By contrast, the luciferase activity increased in cells expressing anti-miR-30c (FIG. 2I). When the 3'-UTR was mutated in this construct the effects of miR-30c and anti-miR-30c were abolished (FIG. 2J). Therefore, miR-30c binds to the 3'-UTR of MTP and induces mRNA degradation leading to reduced MTP activity and apoB secretion.

miR-30c Reduces Cholesterol and Triglycerides in VLDL/LDL Plasma Fractions in Mice Fed Standard Western Diet.

The inventors then explored in vivo physiologic consequences of miR-30c expression. The inventors studied the effect of different miRs on plasma lipoproteins, AST (aspartate aminotransferase) and ALT (alanine aminotransferase) levels as well as hepatic lipids. C57/B16 mice were transduced with lentiviruses expressing different miRs and provided with ad libitum Western diet. After 3 weeks, hepatic levels of miR-30c were approximately 4-fold higher, compared with Scr mice. miR-30c reduced cholesterol (FIG. 3H) in VLDL/LDL fractions but had no effect on triglyceride (3G), plasma AST (FIG. 3I) and ALT (FIG. 3J) levels. Furthermore, there were no significant differences in hepatic triglyceride (FIG. 3K) and cholesterol (FIG. 3L) in these mice.

miR-30c Reduces Plasma Cholesterol and Plasma Triglycerides Leading to Reduced Hyperlipidemia.

Plasma cholesterol were significantly lower in mice injected with miR-30c mimic and higher in mice expressing anti-miR-30c compared with control mice injected with Scr (FIG. 3A). The amounts of total plasma triglyceride in these animals showed a trend similar to the cholesterol (FIG. 3B).

ApoB lipoprotein precipitation analysis of the plasma showed that miR-30c mainly reduced lipids in non-HDL fractions (FIG. 3H) miR-30c had no effect on liver lipids (FIG. 3K-L) and plasma AST/ALT (FIG. 3I-J), indicating no negative impact on liver health in treated animals. These studies suggest that miR-30c prevents increases in Western diet induced hyperlipidemia whereas anti-miR-30c augments these changes.

miR-30c Reduces Hyperlipidemia by Reducing Hepatic Lipoprotein Production.

To understand mechanisms for reduced hyperlipidemia in miR-30c expressing mice, the inventors studied hepatic lipoprotein production in Western diet fed mice after the inhibition of lipases by P407 to prevent lipoprotein catabolism. Triglyceride production rates were significantly higher in anti-miR-30c (372 mg/dl/h), and lower in miR-30c (119 mg/dl/h) compared with Scr (205 mg/dl/h) expressing mice (FIG. 3D). Cholesterol production rates were not affected in miR-30c expressing mice and were increased in anti-miR-30c expressing mice (FIG. 3C). These studies indicate that reduced hyperlipidemia in miR-30c expressing mice might be secondary to decreased hepatic lipoprotein production.

miR-30c Reduction of Plasma Lipids Occurs Specifically Through MTP.

miRs may regulate expression of several genes and modulate multiple pathways. Therefore, the inventors evaluated the specific need of MTP in the reduction of hyperlipidemia by miR-30c by transducing liver-specific MTP knockout (Alb-Cre-Mttp$^{fl/fl}$, L-MTP$^{-/-}$) mice with lentiviruses expressing different miRs miR-30c and anti-miR-30c did not affect plasma triglyceride (FIG. 3E) and cholesterol (FIG. 3F) in L-MTP$^{-/-}$ mice, indicating that reductions in plasma lipids by miR-30c requires MTP expression.

miR-30c Targets More than One Gene Involved in Lipid Metabolism.

To understand reasons for decreased lipid synthesis, Gene Ontology analysis was performed for miR-30c target genes. This analysis revealed that miR-30c is predicted to affect several pathways in lipid metabolism, such as pathways for biosynthesis of steroids, glycerolipids, phospholipids, and fatty acids (FIG. S5A), by targeting several genes involved in these pathways (FIG. S5B). The inventors found that expression of miR-30c in Huh-7 cells reduced mRNA levels of several of these target genes, including LPGAT1, ELOVL5, MBOAT1, and StARD3 (FIG. S5C). Thus, miR-30c appears to coordinately decrease lipid biosynthesis and lipoprotein assembly/secretion to avoid steatosis and lower plasma lipids.

miR-30c Prevents Progression of Atherosclerosis.

Figure 4:
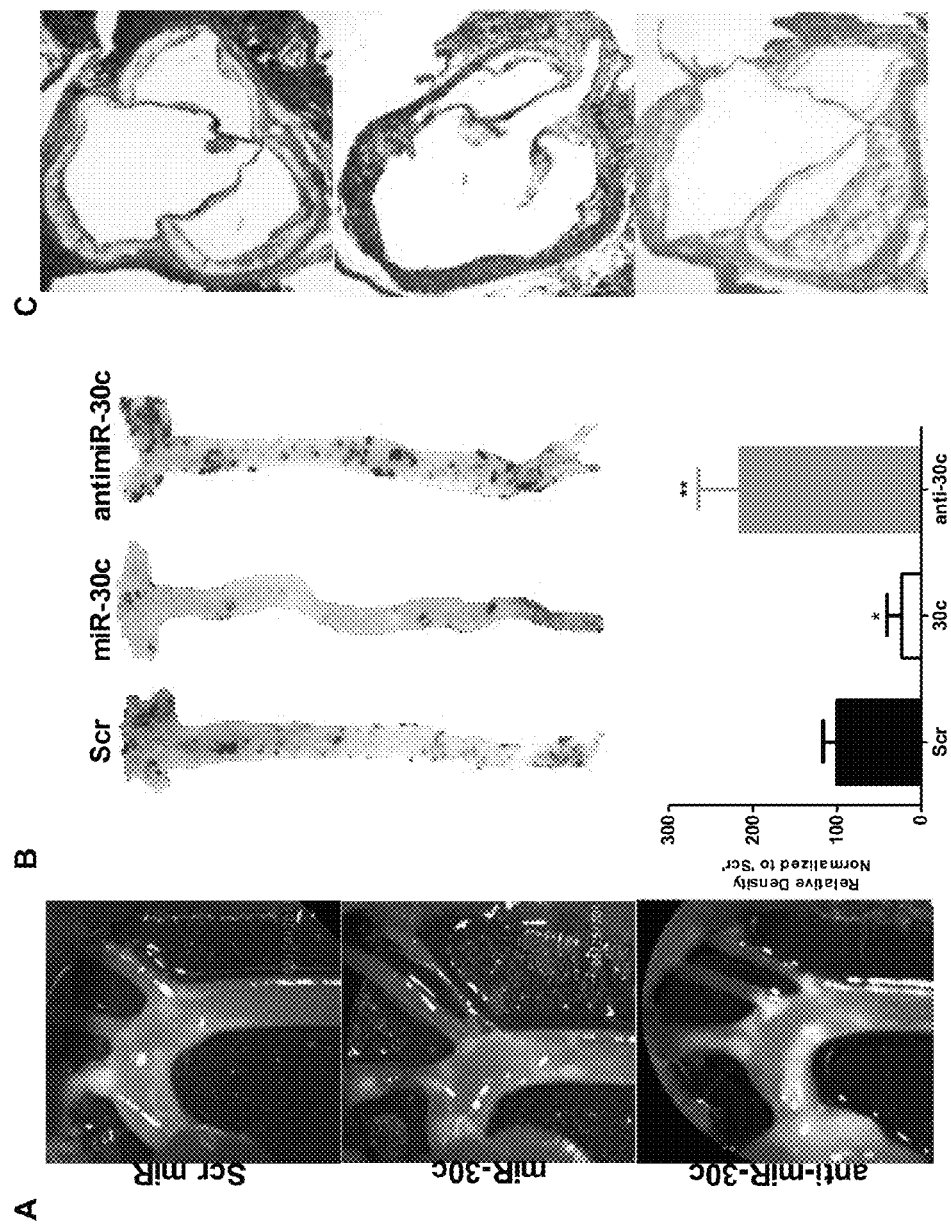
FIG. 4: Effect of miR-30c on atherosclerosis: Female Apoe$^{-/-}$ mice were injected with lentiviruses expressing miR-30c, anti-miR-30c or Scr and started on a Western diet. On week 5, aortic arches were exposed and photographed (A). Whole aortas (B) and aortic root sections (C) were dissected and stained with Oil red O or Hematoxylin and eosin stain, respectively.

Female Apoe$^{-/-}$ mice were injected with different miRs and fed a Western diet for 5 weeks (FIG. 4). Visualization of atherosclerotic plaques at the aortic arch on week 7 indicated that miR-30c expressing mice had smaller lesions compared to control mice injected with Scr (FIG. 4A). In contrast, mice expressing anti-miR-30c had more lesions. Additionally, whole aortas were stained with Oil Red O (FIG. 4B). The lipid staining was less in miR-30c and more in anti-miR-30c expressing mice compared with Scr mice. Similarly, Hematoxylin and eosin stain of the aortic sections reveal small plaque sizes in miR-30c group. (FIG. 4C). Similar results were obtained in a different experiment where miRs were injected. Plasma cholesterol and triglyceride were measured in Apoe$^{-/-}$ mice for 6 weeks (FIG. S3A-B). In addition, plasma transaminases (AST and ALT) were also measured (FIG. S3C-D). Virus was injected into the retro-orbital part of the eye in mice. All animal handling measures and viral injections were done according to and approved by SUNY Downstate Animal Care Facility Immediately afterward, mice were started on a Western diet. These studies indicate that miR-30c protects against, and anti-miR-30c augments, atherosclerosis in Apoe$^{-/-}$ mice.

miR-30c is Regulated by Post-Transcriptional Processing of miR-30c mRNA.

Figure 5:
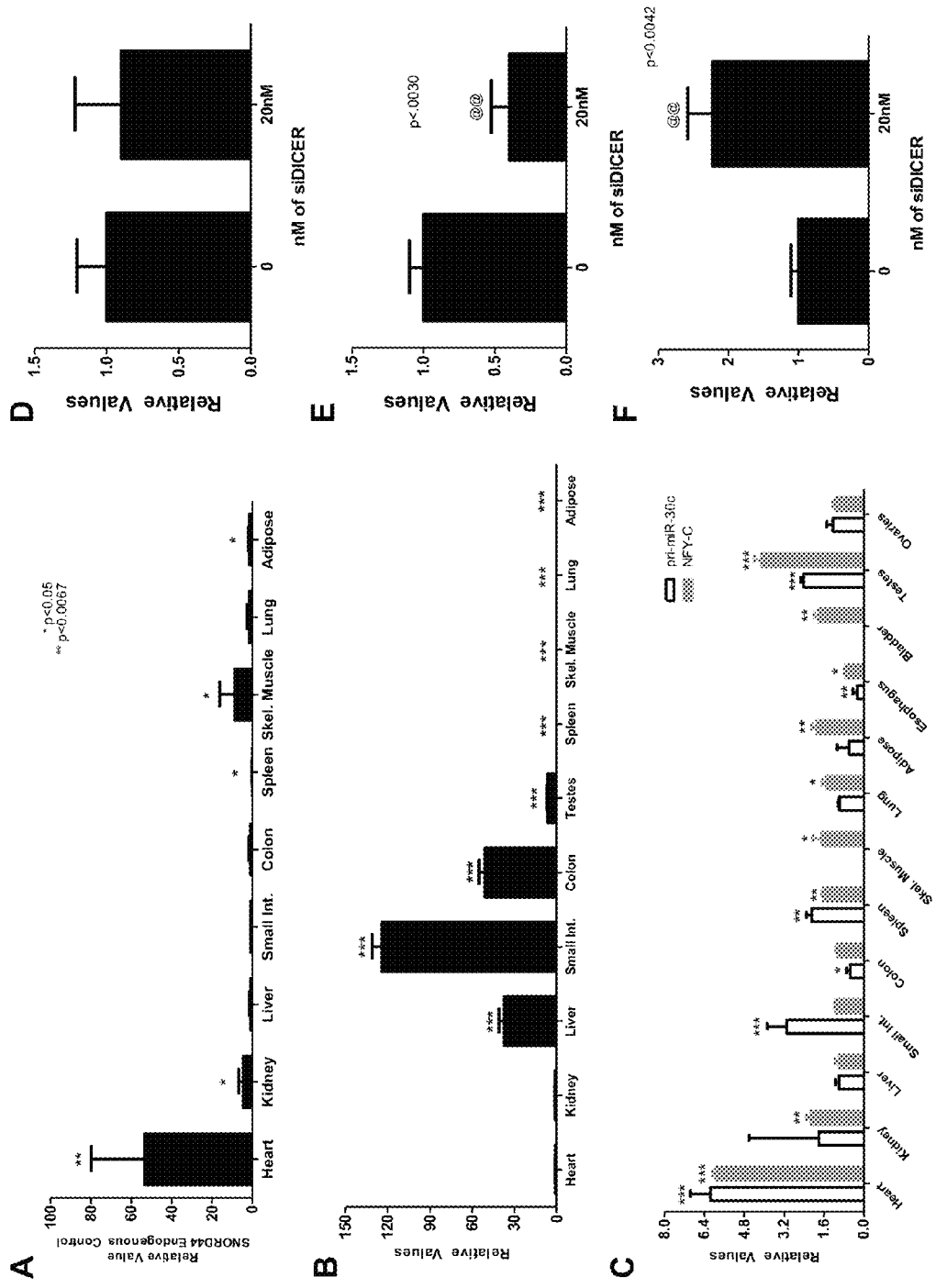
FIG. 5: Expression of miR-30s, MTP and NFY-C in human tissues: (A-C) Abundance of different miRs (A) was measured in indicated human tissues from the First Choice Human Total RNA Survey Panel (Applied Biosystems) by qRT-PCR and normalized to SNORD44. Values in liver were normalized to 1. MTP (B) and NFY-C (C) mRNA, and pri-miR-30c (C) levels were assessed by qRT-PCR and normalized to ARPp0. For MTP (B) and pri-miR-30c/NFY-C values in heart and liver, respectively, were adjusted to 1. (D-F) Huh-7 cells were transfected with indicated amounts of siDICER duplex and levels of pri-miR-30c (D), miR-30c (E), and MTP mRNA (F) were measured after 18 hr. For pri-miR-30c (D) and MTP (F), ARPp0 served as control. For miR-30c, U6 was used as an endogenous control. * p<0.05;  p<0.01, * p<0.001, **** p<0.0001; significance calculated by one-way ANOVA.

Experiments were then performed to understand the regulation of miR-30c synthesis. Tissue expression studies revealed that miR-30b, miR-30c and miR-30e (FIG. 5A) are highly expressed in human heart and skeletal muscle. Notably, their levels were low in the intestine and liver, tissues that highly express MTP (FIG. 5B), indicating a negative relationship between these miRNAs and MTP. miR-30c resides in the intron 5 of the human gene nuclear transcription factor Y subunit C (NFY-C) and is conserved in vertebrates (FIG. S2). NFY-C was ubiquitously expressed with high levels in the heart and testes (FIG. 5C). This expression pattern was very different than that of miR-30c (FIG. 5A). Different steady state levels of the host gene and intronic miR-30c indicated that their expression might be regulated differently involving transcription or post-transcriptional mechanisms.

To further identify mechanisms for regulation of miR-30c, the inventors measured expression of pri-miR-30c in human tissues. Pri-miR-30c expression levels were similar to those of NFY-C indicating that both are transcribed simultaneously and tissue levels of miR-30c might be regulated at posttranscriptional levels (FIG. 5C). To test this hypothesis, Huh-7 cells were treated with siDICER and the amounts of pri-miR-30c, miR-30c, and MTP transcripts were measured. siDICER reduced dicer mRNA levels by 90%. siDICER had no significant effect on pri-miR-30c (FIG. 5D) but reduced miR-30c levels (FIG. 5E). Moreover, siDICER increased MTP mRNA (FIG. 5F). The inventors interpret these data to suggest that NFY-C and pri-miR30c are co-transcribed and the steady state tissue levels of NFY-C and miR-30c differ mainly due to post-transcriptional processing of pri-miR-30c. Reductions in miR-30c accompany increases in MTP mRNA levels. MicroRNAs that potentially bind to MTP mRNA were analyzed using a database called TargetScan. The results of that analysis revealed that a family of microRNAs (miR-30) potentially bind to MTP mRNA 3' UTR. The binding site on MTP mRNA 3' UTR is also evolutionary conserved in vertebrates (FIG. S1). MicroRNA-30c, in and of itself, is also conserved in vertebrates as well (FIG. S2).

Regulation of miR-30c occurs independently of changes in plasma lipid levels and other mechanisms that regulate MTP expression. The inventors then considered the possibility that MTP might reciprocally regulate miR-30c expression and measured miR-30c levels in the livers of Mttp$^{fl/fl}$ and L-MTP$^{-/-}$ mice (FIG. S4A) miR-30c levels were similar in the liver of these mice suggesting that MTP expression does not affect miR-30c expression. Next, the inventors hypothesized that miR-30c might be regulated by changes in plasma lipid levels. However, treatment with a PPARα agonist, or treatment with a PPAR-gamma agonist simultaneously on a Western diet had no effect on miR-30c levels (FIG. S4B-C). Therefore, miR-30c is not regulated by several common mechanisms known to regulate MTP expression. Identification of additional pathways and modifiers that regulate miR-30c can elucidate additional components involved in lipid metabolism.

miR-30c Reduces MTP Activity without Side Effects Associated with MTP Inhibition.

These studies provide evidence that miR30c enhances degradation of MTP mRNA and reduces protein and activity resulting in reduced production of apoB-lipoproteins and lowering of plasma lipids. No side effects associated with other forms of MTP inhibition were noted, possibly because low levels of MTP reduction is effective for beneficial effect without causing liver damage. Hence, treatment with miR-30c is found to be a novel approach to lower plasma lipids.

miR-30c Antagonist Increases ApoB Secretion.

Figure 3:
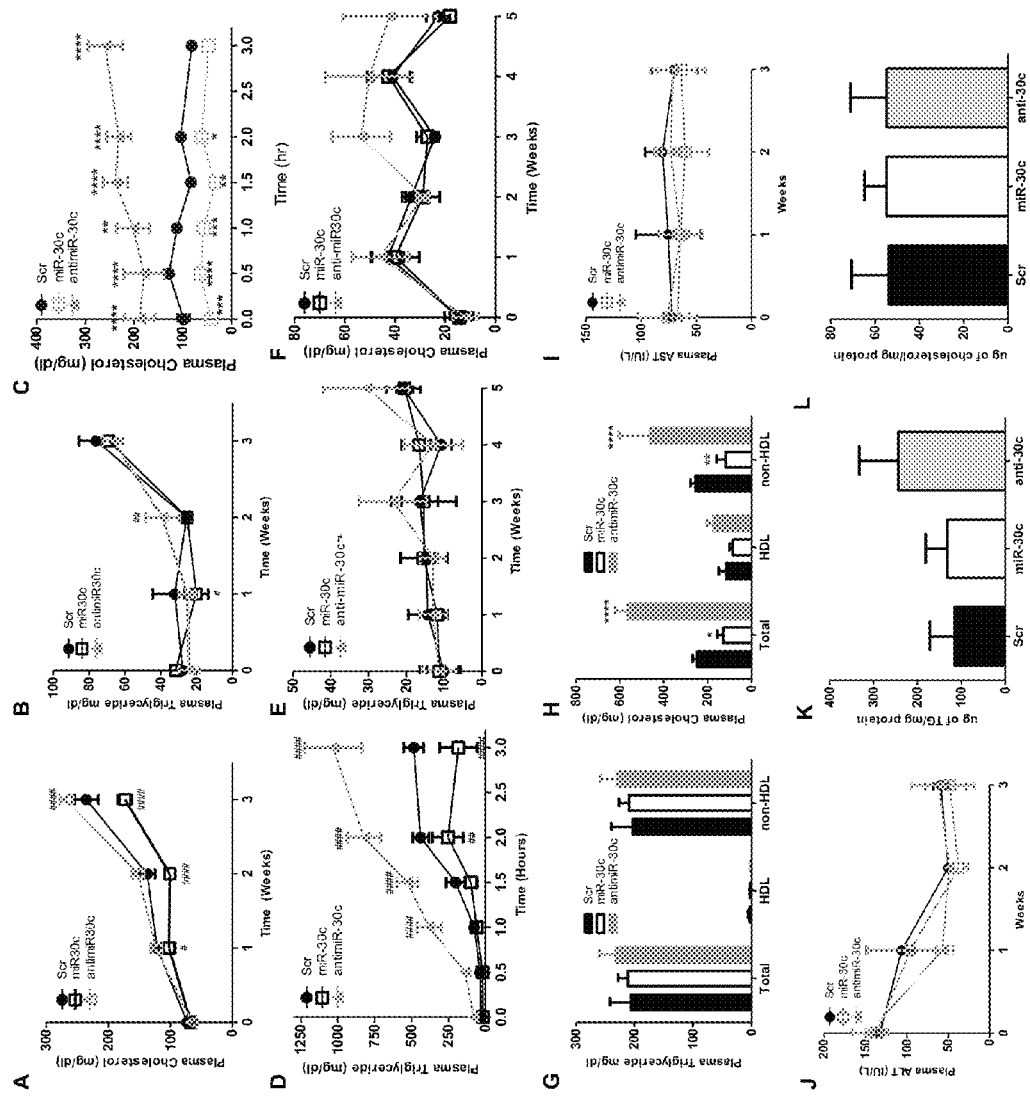
FIG. 3: Effect of miR-30c on plasma lipids in mice: Male CB57/B16 mice (5/group) were injected ($10^8$ infectious units/mouse) retro-orbitally with lentiviruses that express miR-30c, anti-miR-30c or Scr and started on a Western diet. Every week mice were fasted for 4 h and blood was collected to measure total cholesterol (A) and triglyceride (B) for 3 weeks. In a separate experiment, at week 5, after blood collection for plasma lipids, mice were injected with P407 and small blood samples were collected at indicated times to measure cholesterol (C) and triglyceride (D) secretion rates. Slopes between one and 2 h were used to calculate production rates. Liver specific MTP knockout mice (L-MTP$^{-/-}$) were injected with miR-30c, anti-miR-30c or Scr expressing lentiviruses and started on a Western diet. Plasma was collected at weekly intervals to measure changes in triglyceride (E) and cholesterol (F). Plasma triglyceride (G) and cholesterol (H) were measured on HDL and non-HDL fractions of wild-type C57/B16 mice after 3 weeks. Plasma transaminases, AST (I) and ALT (J) were measured every week for 3 weeks. Hepatic levels of (K) triglyceride and (L) cholesterol were measured in these livers.

Anti-miR-30c is expected to bind endogenous miR-30c and reverse its effects. In this study, anti-miR-30c modestly increased MTP mRNA but highly increased apoB secretion in Huh-7 cells (FIG. 1) and in mice (FIG. 3). However, it had modest effect on plasma lipids in L-MTP$^{-/-}$ mice. The modest effects of anti-miR-30c on MTP expression might be secondary to low levels of miR-30c expression. However, stronger effects on apoB secretion suggest that anti-miR-30c might, besides affecting MTP expression, also affect additional proteins that are critical for apoB secretion. Blast analysis revealed that anti-miR30c could potentially bind to miR-30b and therefore, it might provide additional protection against apoB degradation and promote its secretion. However, it should be pointed out that the anti-miR-30c effects do require MTP expression as its effects on apoB levels were not seen in L-MTP$^{-/-}$ mice. Therefore, anti-miR-30c could affect apoB levels by two mechanisms; one involves its inhibition of miR-30c and the other involves inhibition of another protein/mechanism leading to synergistic increase in apoB secretion.

Specificity of miR-30c for MTP.

All the miR-30 family members contain the same seed sequence (FIG. S1). They differ with regards to the compensatory binding sites. MiR-30c has the maximum compensatory binding sites in the MTP transcript. The usage of the phrase 'compensatory binding sites' refers to the miR-30c sequence in and of itself. As defined earlier in this document, microRNA-30c contains a seed sequence that is evolutionary conserved. It is thought that the seed sequence has strongest affinity for its target mRNA. The compensatory binding sites only assist and improve the fidelity of the microRNA to its target. With that said, microRNAs do not have 100% fidelity to its target binding site. However, increased compensatory binding sites implies increased fidelity for its target; hence, better binding and targeting. Compensatory binding sites are any number of bases downstream from the seed sequence. The maximum number of compensatory binding sites is limited to the sequence length of the microRNA itself. For example, if a microRNA has 100% sequence complementarity to its target, one can say that all compensatory binding sites are used. Although it is possible that other miR-30 family members might affect MTP expression under different experimental conditions, the inventors interpret these results to suggest that, besides the seed sequence, compensatory binding sites might also play a role in mRNA degradation. Possibly, specificity of miRs to bind a particular mRNA target can be enhanced by increasing the fidelity of their binding to these compensatory binding sites.

In summary, the inventors have provided evidence that miR-30c reduces MTP mRNA, protein and activity. Further, the inventors have shown that MTP mRNA is degraded faster in the presence of miR-30c. This accelerated degradation is due to the binding of miR-30c to the 3'-UTR of MTP. Further, the inventors have shown that miR-30c lowers plasma triglyceride and cholesterol levels by reducing triglyceride production rates in hyperlipidemia mice. In another study the inventors observed that atherosclerotic plaques are smaller in Apoe$^{-/-}$ mice expressing miR-30c. Taken together, the inventors have provided evidence that miR-30c reduces plasma lipids and atherosclerosis by reducing MTP expression. High fiber foods such as unprocessed whole grains, vegetables, and fruits, are encouraged. Foods rich in fiber, both soluble and insoluble fiber, prevent the re-absorption of cholesterol-rich bile acids from the small intestines back into circulation, thereby reducing circulating cholesterol. Thus, high-fiber, unprocessed foods inhibit cholesterol absorption and lower cholesterol in the body. The patient may also consume fiber supplements, such as Metamucil™ or Benefiber™, to increase dietary fiber intake.

REFERENCE LIST

1. Fernandez-Hernando, C., Suarez, Y., Rayner, K. J., and Moore, K. J. (2011) *Curr. Opin. Lipidol.* 22, 86-92
2. Moore, K. J., Rayner, K. J., Suarez, Y., and Fernandez-Hernando, C. (2011) *Annu. Rev. Nutr.* 31, 49-63
3. Hussain, M. M., Rava, P., Pan, X., Dai, K., Dougan, S. K., Iqbal, J., Lazare, F., and Khatun, I. (2008) *Curr. Opin. Lipidol.* 19, 277-284
4. Hussain, M. M., Shi, J., and Dreizen. P. (2003) *J. Lipid Res.* 44, 22-32
5. Wetterau, J. R., Aggerbeck, L. P., Bouma, M.-E., Eisenberg, C., Munck, A., Hermier, M., Schmitz, J., Gay, G., Rader, D. J., and Gregg, R. E. (1992) *Science* 258, 999-1001
6. Berriot-Varoqueaux, N., Aggerbeck, L. P., Samson-Bouma, M., and Wetterau, J. R. (2000) *Annu. Rev. Nutr.* 20, 663-697
7. Raabe, M., Flynn, L. M., Zlot, C. H., Wong, J. S., Véniant, M. M., Hamilton, R. L., and Young, S. G. (1998) *Proc. Natl. Acad. Sci. U.S.A.* 95, 8686-8691
8. Wetterau, J. R., Gregg, R. E., Harrity, T. W., Arbeeny, C., Cap, M., Conolly, F., Chu, C.-H., George, R. J., Gordon, D. A., Jamil, H., Jolibois, K. G., Kunselman, L. K., Lan, S.-J., Maccagnan, T. J., Ricci, B., Yan, M., Young, D., Chen, Y., Fryszman, O. G., Logan, J. V. H., Musial, C. L., Poss, M. A., Robl, J. A., Simpkins, L. M., Slusarchyk, W. A., Sulsky, R., Taunk, P., Magnin, D. R., Tino, J. A., Lawrence, R. M., Dickson, J. K., Jr., and Biller, S. A. (1998) *Science* 282, 751-754
9. Hussain, M. M. and Bakillah, A. (2008) *Curr. Opin. Lipidol.* 19, 572-578
10. Chang, G., Ruggeri, R. B., and Harwood, H. J., Jr. (2002) *Curr. Opin. Drug Discov. Devel.* 5, 562-570
11. Lee, R. C., Feinbaum, R. L., and Ambros, V. (1993) *Cell* 75, 843-854
12. Ventura, A. and Jacks, T. (2009) *Cell* 136, 586-591
13. Bartel, D. P. (2004) *Cell* 116, 281-297
14. Najafi-Shoushtari, S. H., Kristo, F., Li, Y., Shioda, T., Cohen, D. E., Gerszten, R. E., and Naar, A. M. (2010) *Science* 328, 1566-1569
15. Rayner, K. J., Suarez, Y., Davalos, A., Parathath, S., Fitzgerald, M. L., Tamehiro, N., Fisher, E. A., Moore, K. J., and Fernandez-Hernando, C. (2010) *Science* 328, 1570-1573
16. Marquart, T. J., Allen, R. M., Ory, D. S., and Baldan, A. (2010) *Proc. Natl. Acad. Sci. U.S.A* 107, 12228-12232
17. Gerin, I., Clerbaux, L. A., Haumont, O., Lanthier, N., Das, A. K., Burant, C. F., Leclercq, I. A., Macdougald, O. A., and Bommer, G. T. (2010) *J. Biol. Chem.*
18. Horie, T., Ono, K., Horiguchi, M., Nishi, H., Nakamura, T., Nagao, K., Kinoshita, M., Kuwabara, Y., Marusawa, H., Iwanaga, Y., Hasegawa, K., Yokode, M., Kimura, T., and Kita, T. (2010) *Proc. Natl. Acad. Sci. U.S.A* 107, 17321-17326
19. Rava, P. and Hussain, M. M. (2007) *Biochemistry* 46, 12263-12274
20. Chang, B. H. J., Liao, W., Li, L., Nakamuta, M., Mack, D., and Chan, L. (1999) *J. Biol. Chem.* 274, 6051-6055
21. Athar, H., Iqbal, J., Jiang, X. C., and Hussain, M. M. (2004) *J. Lipid Res.* 45, 764-772
22. Rava, P., Athar, H., Johnson, C., and Hussain, M. M. (2005) *J. Lipid Res.* 46, 1779-1785
23. Hussain, M. M., Zhao, Y., Kancha, R. K., Blackhart, B. D., and Yao, Z. (1995) *Arterioscler. Thromb. Vasc. Biol.* 15, 485-494
24. Bakillah, A., Zhou, Z., Luchoomun, J., and Hussain, M. M. (1997) *Lipids* 32, 1113-1118

What is claimed is:

1. A method for treating cardiovascular disease, hyperlipidemia, atherosclerosis, obesity, diabetes, or metabolic syndrome in a subject in need thereof, comprising administration of miR-30c or a miR-30c agonist in an amount effective to treat the disease in said subject wherein administration of the miR-30c or a miR-30c agonist results in avoidance of hepatic steatosis in said subject.

2. A method for reducing serum lipids in a subject in need thereof, comprising administration of miR-30c or a miR-30c agonist in an amount effective to reduce serum lipids in said subject wherein administration of the miR-30c or a miR-30c agonist results in avoidance of hepatic steatosis in said subject.

3. A method for reducing microsomal triglyceride transfer protein (MTP) activity in a subject in need thereof, comprising administration of miR-30c or a miR-30c agonist in an amount effective to reduce MTP activity in said subject wherein administration of the miR-30c or a miR-30c agonist results in avoidance of hepatic steatosis in said subject.

4. A method for reducing lipid or lipoprotein biosynthesis in a subject in need thereof, comprising administration of miR-30c or a miR-30c agonist in an amount effective to reduce lipid or lipoprotein biosynthesis wherein administration of the miR-30c or a miR-30c agonist results in avoidance of hepatic steatosis in said subject.

5. The method of claim 1, further comprising administration of at least one additional cholesterol reducing agent.

6. The method of claim 5, wherein one of the at least one additional cholesterol reducing agents is a statin.

7. The method of claim 2, further comprising administration of at least one additional cholesterol reducing agent.

8. The method of claim 7, wherein one of the at least one additional cholesterol reducing agents is a statin.

9. The method of claim 4, further comprising administration of at least one additional cholesterol reducing agent.

10. The method of claim 9, wherein one of the at least one additional cholesterol reducing agents is a statin.

11. A method for treating a disease or disorder selected from the group consisting of cardiovascular disease, hyperlipidemia, atherosclerosis, obesity, diabetes, or metabolic syndrome in a subject in need thereof, comprising administration of miR-30c or a miR-30c agonist in an amount effective to reduce the levels of at least one target gene selected from the group consisting of LPGAT1, ELOVL5, MBOAT, IFG1R, ATP8B1, ALG9, LEPR, CHKA, PPARGC1A and StARD3 in said subject, wherein administration of the miR-30c or a miR-30c agonist results in treatment of the disease or disorder.

12. The method of claim 11, wherein administration of the miR-30c or a miR-30c agonist results in avoidance of steatosis.

13. A method for reducing serum lipids in a subject in need thereof, comprising administration of miR-30c or a miR-30c agonist in an amount effective to reduce the levels of at least one target gene selected from the group consisting of LPGAT1, ELOVL5, MBOAT, IFG1R, ATP8B1, ALG9, LEPR, CHKA, PPARGC1A and StARD3 in said subject, wherein administration of the miR-30c or a miR-30c agonist results in reducing serum lipids in said subject.

14. The method of claim 13, wherein administration of the miR-30c or a miR-30c agonist results in avoidance of steatosis.

15. A method for reducing microsomal triglyceride transfer protein (MTP) activity in a subject in need thereof, comprising administration of miR-30c or a miR-30c agonist in an amount effective to reduce the levels of at least one target gene selected from the group consisting of LPGAT1, ELOVL5, MBOAT, IFG1R, ATP8B1, ALG9, LEPR, CHKA, PPARGC1A and StARD3 in said subject, wherein administration of the miR-30c or a miR-30c agonist results in reduced MTP activity in said subject.

16. The method of claim 15, wherein administration of the miR-30c or a miR-30c agonist results in avoidance of steatosis.

17. A method for reducing lipid or lipoprotein biosynthesis in a subject in need thereof, comprising administration of miR-30c or a miR-30c agonist in an amount effective to reduce the levels of at least one target gene selected from the group consisting of LPGAT1, ELOVL5, MBOAT, IFG1R, ATP8B1, ALG9, LEPR, CHKA, PPARGC1A and StARD3 in said subject, wherein administration of the miR-30c or a miR-30c agonist results in reduced lipid or lipoprotein biosynthesis in said subject.

18. The method of claim 17, wherein administration of the miR-30c or a miR-30c agonist results in avoidance of steatosis.

* * * * *